United States Patent
Gaur et al.

(10) Patent No.: US 6,251,396 B1
(45) Date of Patent: *Jun. 26, 2001

(54) METHODS FOR TREATMENT OF MULTIPLE SCLEROSIS USING PEPTIDE ANALOGS OF HUMAN MYELIN BASIC PROTEIN

(75) Inventors: Amitabh Gaur, San Diego; Paul Conlon, Solana Beach; Nicholas C. Ling, San Diego, all of CA (US); Theophil Staehelin, Arlesheim (CH); Paul D. Crowe, Encinitas, CA (US)

(73) Assignees: Neurocrine Biosciences, Inc., San Diego, CA (US); Novartis AG, Basel (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/137,759

(22) Filed: Aug. 20, 1998

Related U.S. Application Data

(63) Continuation-in-part of application No. 08/342,408, filed on Nov. 18, 1994.

(51) Int. Cl.$^7$ .......................... A61K 39/00; A61K 38/17; C07K 7/08; C07K 14/47

(52) U.S. Cl. ............................ 424/184.1; 514/2; 514/13; 530/300; 530/325; 530/326

(58) Field of Search .................................. 514/2, 13, 903; 424/184.1

(56) References Cited

U.S. PATENT DOCUMENTS

| | | | |
|---|---|---|---|
| 5,559,209 | 9/1996 | Nishimoto | 530/326 |
| 6,036,957 | 3/2000 | Weiner et al. | 424/184.1 |

FOREIGN PATENT DOCUMENTS

| | | |
|---|---|---|
| WO 88/00057 | 1/1988 | (WO) . |
| WO 88/10120 | 12/1988 | (WO) . |
| WO 91/12816 | 9/1991 | (WO) . |
| WO 92/06708 | 4/1992 | (WO) . |
| WO 92/21367 | 12/1992 | (WO) . |
| WO 93/08212 | 4/1993 | (WO) . |
| WO 93/12814 | 7/1993 | (WO) . |
| WO 93/19178 | 9/1993 | (WO) . |
| WO 93/21222 | 10/1993 | (WO) . |
| WO 94/06828 | 3/1994 | (WO) . |
| WO 95/08572 | 3/1995 | (WO) . |
| WO 96/12731 | 5/1996 | (WO) . |
| WO 96/16085 | 5/1996 | (WO) . |
| WO 96/16086 | 5/1996 | (WO) . |
| WO 96/28470 | 9/1996 | (WO) . |
| WO 96/34622 | 11/1996 | (WO) . |
| WO 97/35879 | 10/1997 | (WO) . |

OTHER PUBLICATIONS

Arimilli et al., "Identification of Core Structure and Critical T Cell Receptor Contact Residues in an Antigenic Peptide by Measuring Acidification Rates," *Journal of Immunological Methods* 217:49–59, 1998.

Ausubel et al., "Changes in Cytokine Secretion Induced by Altered Peptide Ligands of Myelin Basic Protein Peptide 85–99," *Journal of Immunology* 159:2502–2512, 1997.

Abstract 65027 from Biol. Abstr. 81(7): AB–701 (1985) of the article "Monoclonal antibodies to human myelin basic protein," *J. Neurochem.* 46(1): 47–53, 1985.

Acha–Orbea et al., "Limited Heterogeneity of T Cell Receptors from Lymphocytes Mediating Autoimmune Encephalomyelitis Allows Specific Immune Intervention," *Cell* 54: 263–273, 1988.

Antel et al., "Vaccination with an altered MBP Peptide Induces a Persistent Immune Response," *Journal of Neuroimmunology* 90(1): p. 18, Abstract No. 80, 1998.

Babbitt et al., "Antigenic competition at the level of peptide–Ia–binding," *Proc. Natl. Acad. Sci. USA* 83: 4509–4513, 1986.

Bellacosa et al., "A Retroviral Oncogen, akt, Encoding a Serine–Threonine Kinase Containing an SH2–Like Region," *Science* 254(5029): 274–277, 1991.

Bernard, "Experimental Autoimmune Encephalomyelitis in Mice: Genetic Control of Susceptibility," *Journal of Immunogenetics* 3: 263–274, 1976.

Brocke et al., "In Vitro Proliferative Responses and Antibody Titers Specific to Human Acetycholine Receptor Synthetic Peptides in Patients with Myasthenia Gravis and Relation to HLA Class II Genes," *J. Clin. Invest.* 82: 1894–1900, 1988.

Brocke et al., "Treatment of experimental encephalomyelitis with a peptide analogue of myelin basic protein," *Nature* 379: 343–346, 1996.

Brostoff and Howell, "T Cell Receptors, Immunoregulation, and Autoimmunity," *Clinical Immunology and Immunopathology* 62(1): 1–7, 1992.

Carter and Rodriguez, "Immunosuppressive Treatment of Multiple Sclerosis," *Mayo Clin. Proc.* 64: 664–669, 1989.

Chou et al., "Identity of Myelin Basic Protein from Multiple Sclerosis and Human Control Brains: Discovery of a Genetic Variant," *Journal of Neurochemistry* 30: 745–750, 1978.

(List continued on next page.)

Primary Examiner—Michael Borin
(74) Attorney, Agent, or Firm—Seed Intellectual Property Law Group PLLC

(57) ABSTRACT

The present invention is directed toward peptide analogs of human myelin basic protein. The peptide analog is at least seven amino acids long and derived from residues 83 to 99 of human myelin basic protein. The analogs are altered from the native sequence at least at positions 91, 95, or 97. Additional alterations may be made at other positions. Pharmaceutical compositions containing these peptide analogs are provided. The peptide analogs are useful for treating multiple sclerosis.

3 Claims, 15 Drawing Sheets

OTHER PUBLICATIONS

Day et al., "The Polyclonal Antibody Responses of Lewis Rats to the Synthetic Encephalitogenic Neuropeptide S55S (Residues 72–84 of Guinea Pig Myelin Basic Protein) and Its Analogs," *Journal of Neuroscience Research 18*: 214–221, 1987.

Einstein et al., "Suppression of Experimental Allergic Encephalomyelitis By Chemically Modified Encephalitogen," *Immunochemistry 9*: 1013–1019, 1972.

Evavold and Allen, "Separation of IL–4 Production from Th Cell Proliferation by an Altered T Cell Receptor Ligand," *Science 252*: 1308–1310, 1991.

Gammon et al., "Neonatal T–cell tolerance to minimal immunogenic peptides is caused by clonal inactivation," *Nature 319*: 413–415, 1986.

Gaur et al., "Amelioration of relapsing experimental autoimmune encephalomyelitis with altered myelin basic protein peptides involves different cellular mechanisms," *Journal of Neuroimmunology 74*: 149–158, 1997.

Gaur et al., "Amerlioration of Autoimmune Encephalomyelitis by a Myelin Basic Protein Synthetic Peptide–Induced Anergy," *Science (258)*: 1491–1494, 1992.

Gautam et al., "A Polyalanine Peptide With only Five Native Myelin Basic Protein Residues Induces Autoimmune Encephalomyelitis," *J. Exp. Med. 176*: 605–609, 1992.

Gautam et al., "Inhibition Of Experimental Autoimmune Encephalomyelitis By A Nonimmunogenic Non–Self Peptide That Binds to I–A$^{u1}$," *The Journal of Immunology 148*(10): 3049–3054, 1992.

Hadden et al., "Thymic Hormones, Interleukins, Endotoxin and Thymomimetic Drugs in T Lymphocyte Ontogeny," in *Advances in Immunopharmacology 3*, L. Chedid et al. (Eds.), 1985, pp. 487–497.

Hashim, "Experimental Allergic Encephalomyelitis: Activation of Suppressor T Lymphocytes by a Modified Sequence of the T Effector Determinant," *Journal of Immunology 126*(2): 419–423, 1981.

Hashim and Day, "Synthetic Peptide Analogs to Probe the Immunological Expression of the Rat Encephalitogenic Neuropeptide," *Journal of Neuroscience Research 18*: 209–213, 1987.

Hashim et al., "Suppression and Reversal of Allergic Encephalomyelitis in Guinea Pigs with a Non–Encephalitogenic Analogue of the Tryptophan Region of the Myelin Basic Protein," *Journal of Immunology 116*(1): 126–130, 1976.

Jahnke et al., "Sequence Homology Between Certain Viral Proteins and Proteins Related to Encephalomyelitis and Neuritis," *Science 229*: 282–284, 1985.

Kardys and Hashim, "Experimental Allergic Encephalomyelitis in Lewis Rats: Immunoregulation of Disease By a Single Amino Acid Substitution in the Disease–Inducing Determinant," *Journal of Immunology 127*(3): 862–866, 1981.

Karin et al., "Reversal of Experimental Autoimmune Encephalomyelitis by a Soluble Peptide Variant of a Myelin Basic Protein Epitope: T Cell Receptor Antagonism and Reduction of Interferon γ and Tumor Necrosis Factor α Production," *J. Exp. Med. 180*: 2227–2237, 1994.

Kira et al., "Experimental Allergic Encephalomyelitis in Rabbits. A Major Encephalitogenic Determinant within Residues 1–44 of Myelin Basic Protein," *J. of Neuroimmunol. 12*(3): 183–193, 1986.

Kuchroo et al., "A Single TCR Antagonist Peptide Inhibits Experimental Allergic Encephalomyelitis Mediated by a Diverse T Cell Repertoire," *Journal of Immunology 153*: 3326–3336, 1994.

Lamont et al., "Inhibition of Experimental Autoimmune Encephalomyelitis Induction In SJL/J Mice Using A Peptide With High Affinity For IA$^S$ Molecules," *Journal of Immunology 145*(6): 1687–1693, 1990.

Lehninger, "The Amino Acid Building Blocks of Proteins," in *Biochemistry*, 2$^{nd}$ ed., Worth Publishers, Inc. pp. 71–75, 1975.

Lindsey et al., "Double–Blind, Randomized, Placebo–Controlled Evaluation of the Safety, Tolerability, and Pharmacokinetics of CGP 77116 in Patients with Multiple Sclerosis," *Neurology 50*: Abstract 149, 1998.

Martin et al., "A Myelin Basic Protein Peptide is Recognized by Cytotoxic T Cells in the Contect of Four HLA–DR Types Associated with Multiple Sclerosis," *Journal of Experimental Medicine 173*: 19–24, 1991.

Martin et al., "Diversity in Fine Specificity and T Cell Receptor Usage of the Human CD4+ Cytotoxic T Cell Response Specific for the Immunodominant Myelin Basic Protein Peptide 87–106," *Journal of Immunology 148*(5): 1359–1366, 1992.

Martin et al., "Immunological Aspects of Demyelinating Diseases," *Annu. Rev. Immunol. 10*: 153–187, 1992.

Pautot et al., "Leucine aminopeptidase: An inducible component of the defense response in *Lycopersicon esculentum* (tomato)," *Proc. Natl. Acad. Sci. USA 90*: 9906–9910, 1993.

Raine and Stone, "Animal Model for Multiple Sclerosis. Chronic experimental allergic encephalomyelitis in inbred guinea pigs," *New York State Journal of Medicine/September:* 1693–1697, 1977.

Rothbard, "Peptides and the Cellular Immune Response," *Ann. Inst. Pasteur/Virologie 137 E*: 518–526, 1986.

Rothbard and Taylor, "A sequence pattern common to T cell epitopes," *EMBO J. 7*(1): 93–100, 1988.

Rudinger, "Characteristics of the amino acids as components of a peptide hormone sequence," in *Peptide Hormones*, J. A. Parsons (ed.), University Park Press, Baltimore, pp. 1–7, 1976.

Sakai et al., "Characterization of a major encephalitogenic T cell epitope in SJL/J mice with synthetic oligopeptides of myelin basic protein," *Journal of Neuroimmunology 19*: 21–32, 1988.

Sakai et al., "Prevention of experimental encephalomyelitis with peptides that block interaction of T cells with major histocompatibility complex proteins," *Proc. Natl. Acad. Sci. USA 86*: 9470–9474, 1989.

Santambrogio et al., "Altered peptide ligand modulation of experimental allergic encephalomyelitis: immune responses within the CNS," *Journal of Neuroimmunology 81*: 1–13, 1998.

Seder and Paul, "Acquisition Of Lymphokine–Producing Phenotype By CD4$^+$ T Cells," *Annu. Rev. Immunol. 12*: 635–673, 1994.

Servis et al., "Two adjacent epitopes on a synthetic dodecapeptide induce lactate dehydrogenase B–specific helper and suppressor T cells," *Proc. R. Soc. Lond. B 228*: 461–470, 1986.

Sette et al., "Analysis of lysozyme–specific immune responses by synthetic peptides. I. Characterization of antibody and T cell–mediated responses to the N–terminal peptide of hen egg–white lysozyme," *Eur. J. Immunol. 16*: 1–6, 1986.

Sloan–Lancaster and Allen, "Significance of T–cell stimulation by altered peptide ligands in T cell biology," *Current Opinion in Immunology 7*: 103–109, 1995.

Sloan–Lancaster et al., "Induction of T–cell anergy by altered T–cell–receptor ligand on live antigen–presenting cells," *Nature 363*: 156–159, 1993.

Smilek et al., "A single amino acid change in a myelin basic protein peptide confers the capacity to prevent rather than induce experimental autoimmune encephalomyelitis," *Proc. Natl. Acad. Sci. USA 88*: 9633–9637, 1991.

Sriram et al., "Administration of Myelin Basic Protein–Coupled Spleen Cells Prevents Experimental Allergic Encephalitis," *Cellular Immunology 75*: 378–382, 1983.

Steinman, "A few autoreactive cells in an autoimmune infiltrate control a vast population of nonspecific cells: A tale of smart bombs and the infantry," *Proc. Natl. Acad. Sci. USA 93*: 2253–2256, 1996.

Steinman, "Autoimmune Disease: Misguided assaults on the self produce multiple sclerosis, juvenile diabetes and other chronic illnesses. Promising therapies are emerging," *Scientific American* : 75–83, 1993.

Steinman, "Multiple Sclerosis: A Coordinated Immunological Attack against Myelin in the Central Nervous System," *Cell 85*: 299–302, 1996.

Steinman et al., "Major T–cell responses in multiple sclerosis," *Molecular Medicine Today 1*: 79–83, 1995.

Steinman et al., "Natural occurrence of thymocytes that react with myelin basic protein," *Neurology 30*(7): 755–759, 1980.

Steinman et al., "Regulation of autosensitization to encephalitogenic myelin basic protein by macrophage–associated and soluble antigen," *Nature 265*: 173–175, 1977.

Steinman et al., "The Epigenetics Of Multiple Sclerosis: Clues to Etiology and a Rationale for Immune Therapy," *Annu. Rev. Neurosci. 17*: 247–265, 1994.

Su et al., "Synthetic Myelin Basic Protein Peptide Analogs Are Specific Inhibitors of Phospholipid/Calcium–Dependent Protein Kinase (Protein Kinase C)," *Biochemical and Biophysical Research Communications 134*(1): 78–84, 1986.

Talmadge et al., "Screening Models for Biological Response Modifiers," in 13$^{th}$ International Congress of Chemotherapy. Symposium, Biological Responses Modifiers; SY 64 part 203, Vienna Aug. 28–Sep. 2, 1993, pp. 203/19–203/34.

Teitelbaum et al., "Specific inhibition of the T–cell response to myelin basic protein by the synthetic copolymer Cop 1," *Proc. Natl. Acad. Sci. USA 85*: 9724–9728, 1988.

Vogt et al., "Ligand Motifs of HLA–DRB5*0101 and DRB1*1501 Molecules Delineated from Self–Peptides," *Journal of Immunology 153*: 1665–1673, 1994.

Weigle, "Analysis of Autoimmunity through Experimental Models of Thyroiditis and Allergic Encephalomyelitis," *Advances In Immunology 30*: 159–273, 1980.

Wisniewski and Keith, "Chronic Relapsing Experimental Allergic Encephalomyelitis: An Experimental Model of Multiple Sclerosis," *Ann. Neurol. 1*: 144–148, 1977.

Wraith et al., "Antigen Recognition in Autoimmune Encephalomyelitis and the Potential for Peptide–Mediated Immunotherapy," *Cell 59*: 247–255, 1989.

Wraith et al., "T Cell Recognition as the Target for Immune Intervention in Autoimmune Disease," *Cell 57*: 709–715, 1989.

Wucherpfennig et al., "Structural Requirements for Binding of an Immunodominant Myelin Basic Protein Peptide to DR2 Isotypes and for Its Recognition by Human T Cell Clones," *J. Exp. Med. 179*: 279–290, 1994.

Zamvil and Steinman, "The T Lymphocyte in Experimental Alleric Encephalomyellitis," *Annu. Rev. Immunol. 8*: 579–621, 1990.

Zamvil et al., "Multiple Discrete Encephalitogenic Epitopes of the Autoantigen Myelin Basic Protein Include a Determinant for I–E Class II Restricted T Cells," *J. Exp. Med. 168*: 1181–1186, 1988.

Zamvil et al., "T–cell clones specific for myelin basic protein induce chronic relapsing paralysis and demyelination," *Nature 317*: 355–358, 1985.

Zamvil et al., "Encephalitogenic T Cell Clones Specific for Myelin Basic Protein," *J. Exp. Med. 162*: 2107–2124, 1985.

Zamvil et al., "T–cell epitope of the autoantigen myelin basic protein that induces encephalomyelitis," *Nature 324*: 258–260, 1986.

Zamvil et al., "T–cell Specificity for Class II(I–A) and the Encephalitogenic N–Terminal Epitope of the Autoantigen Myelin Basic Protein," *Journal of Immunology 139*(4): 1075–1079, 1987.

ATGGCGTCACAGAAGAGACCCTCCCAGAGGCACGGATCCAAGTACCTGGCCACAGCAAGTACCATGGACC
1
M  A  S  Q  K  R  P  S  Q  R  H  G  S  K  Y  L  A  T  A  S  T  M  D

ATGCCAGGCATGGCTTCCTCCCAAGGCACAGAGACACGGGCATCCTTGACTCCATCGGGCGCTTCTTTGG

H  A  R  H  G  F  L  P  R  H  R  D  T  G  I  L  D  S  I  G  R  F  F  G

CGGTGACAGGGGTGCGCCAAAGCGGGGCTCTGGCAAGGACTCACACCACCCGGCAAGAACTGCTCACTAT

G  D  R  G  A  P  K  R  G  S  G  K  D  S  H  H  P  A  R  T  A  H  Y

GGCTCCCTGCCCCAGAAGTCACACGGCCGGACCCAAGATGAAAACCCCGTAGTCCACTTCTTCAAGAACA

G  S  L  P  Q  K  S  H  G  R  T  Q  D  E  N  P  <u>V  V  H  F  F  K  N</u>

TTGTGACGCCTCGCACACCACCCCCGTCGCAGGGAAAGGGGAGAGGACTGTCCCTGAGCAGATTTAGCTG

<u>I  V  T  P  R  T  P</u>  P  P  S  Q  G  K  G  R  G  L  S  L  S  R  F  S  W

GGGGGCCGAAGGCCAGAGACCAGGATTTGGCTACGGAGGCAGAGCGTCCGACTATAAATCGGCTCACAAG

G  A  E  G  Q  R  P  G  F  G  Y  G  G  R  A  S  D  Y  K  S  A  H  K

GGATTCAAGGGAGTCGATGCCCAGGGCACGCTTTCCAAAATTTTTAAGCTGGGAGGAAGAGATAGTCGCT

G  F  K  G  V  D  A  Q  G  T  L  S  K  I  F  K  L  G  G  R  D  S  R

CTGGATCACCCATGGCTAGACGCTGA

```
                      83           90      95      99
                      |            |       |       |
        MBP (83-99)   E N P V V H F F K N I V T P R T P

NBI-5719      a K . . . . . A . A . . . . . a .

NBI-5748      a K . . . . . L . A . . . . . a .

NBI-5765      a . . . . . . A . A . . . . . . .

NBI-5788      a K . . . . . L . A . . . . . . .

NBI-5789      a K . . . . . A . A . . . . . . .
```

METHODS FOR TREATMENT OF MULTIPLE SCLEROSIS USING PEPTIDE ANALOGS OF HUMAN MYELIN BASIC PROTEIN

CROSS-REFERENCE TO RELATED APPLICATIONS

This application is a continuation-in-part of U.S. patent application Ser. No. 08/342,408, filed Nov. 18, 1994.

TECHNICAL FIELD

The present invention relates generally to methods for treating multiple sclerosis by using peptide analogs of human myelin basic protein.

BACKGROUND OF THE INVENTION

Multiple sclerosis (MS) is a chronic, inflammatory disease that affects approximately 250,000 individuals in the United States. Although the clinical course may be quite variable, the most common form is manifested by relapsing neurological deficits, in particular, paralysis, sensory deficits, and visual problems.

The inflammatory process occurs primarily within the white matter of the central nervous system and is mediated by T lymphocytes, B lymphocytes, and macrophages. These cells are responsible for the demyelination of axons. The characteristic lesion in MS is called the plaque due to its macroscopic appearance.

Multiple sclerosis is thought to arise from pathogenic T cells that somehow evaded mechanisms establishing self-tolerance, and attack normal tissue. T cell reactivity to myelin basic protein may be a critical component in the development of MS. The pathogenic T cells found in lesions have restricted heterogeneity of antigen receptors (TCR). The T cells isolated from plaques show rearrangement of a restricted number of $V\alpha$ and $V\beta$ gene segments. In addition, the TCRs display several dominant amino acid motifs in the third complementarity determining region (CDR), which is the major antigen contact site. All together, three CDR3 motifs have been identified in T cell clones known to recognize an epitope within amino acids 82–106 of myelin basic protein. These motifs were found in 44% of rearranged TCR sequences involving one particular $V\beta$ gene rearranged in T cells isolated from brain of two patients with MS.

A definitive treatment for MS has not been established. Historically, corticosteroids and ACTH have been used to treat MS. Basically, these drugs reduce the inflammatory response by toxicity to lymphocytes. Recovery may be hastened from acute exacerbations, but these drugs do not prevent future attacks or prevent development of additional disabilities or chronic progression of MS (Carter and Rodriguez, *Mayo Clinic Proc.* 64:664, 1989; Weiner and Hafler, *Ann. Neurol.* 23:211, 1988). In addition, the substantial side effects of steroid treatments make these drugs undesirable for long-term use.

Other toxic compounds, such as azathioprine, a purine antagonist, cyclophosphamide, and cyclosporine have been used to treat symptoms of MS. Like corticosteroid treatment, these drugs are beneficial at most for a short term and are highly toxic. Side effects include increased malignancies, leukopenias, toxic hepatitis, gastrointestinal problems, hypertension, and nephrotoxicity (Mitchell, *Cont. Clin. Neurol,* 77:231, 1993; Weiner and Hafler, supra). Antibody based therapies directed toward T cells, such as anti-CD4 antibodies, are currently under study for treatment of MS. However, these agents may cause deleterious side effects by immunocompromising the patient.

More recently, cytokines such as IFN-$\gamma$ and IFN-$\beta$ have been administered in attempts to alleviate the symptoms of MS. However, a pilot study involving IFN-$\gamma$ was terminated because 7 of 18 patients treated with this drug experienced a clinical exacerbation within one month after initiation of treatment. Moreover, there was an increase in the specific response to MBP (Weiner and Hafler, supra).

Betaseron, a modified beta interferon, has recently been approved for use in MS patients. Although Betaseron treatment showed some improvement in exacerbation rates (Paty et al., *Neurology* 43:662, 1993), there was no difference in the rate of clinical deterioration between treated and control groups (IFNB MS Study Group, *Neurology* 43:655, 1993; Paty et al., supra). Side effects were commonly observed. The most frequent of such side effects were fever (40%–58% of patients), flu-like symptoms (76% of patients), chills (46% of patients), mylagias (41% of patients), and sweating (23% of patients). In addition, injection site reactions (85%), including inflammation, pain, hypersensitivity and necrosis, were common (IFNB MS Study Group, supra; Connelly, *Annals of Pharm.* 28:610, 1994).

In view of the problems associated with existing treatments of MS, there is a compelling need for improved treatments which are more effective and are not associated with such disadvantages. The present invention exploits the use of peptide analogs which antagonize a T cell response to human myelin basic protein to effectively treat MS, while providing other related advantages.

SUMMARY OF THE INVENTION

The present invention provides peptide analogs comprising at least 7 (preferably consecutive) amino acids selected from residues 83 to 99 of human myelin basic protein in which either L-lysine at position 91, L-threonine at position 95, or L-arginine at position 97 is altered to another amino acid. In one embodiment, the peptide analog comprises at least 7 amino acids selected from residues 83–99, L-lysine at position 91 is altered and one to three additional L-amino acids selected from residues 86, 87, 88, 95, 98 or 99 are altered to another amino acid. In a second related embodiment, L-threonine at position 95 is altered and one to three additional amino acids selected from residues 86, 87, 88, 91, 98 and 99 or 86, 87, 88, 97, 98, and 99 are altered to another amino acid. In a third related embodiment, L-arginine at position 97 is altered and one to three additional amino acids selected from residues 86, 87, 88, 95, 98 or 99 are altered to another amino acid.

Within another set of embodiments, the peptide analog comprises residues 83–99 of human myelin basic protein, wherein the peptide analogs preferably contain two to five alterations. In preferred aspects of the invention, the peptide analogs have altered residues 89, 91, 95 or 97 to alanine and the additional amino acids are altered to the corresponding D-form amino acid.

In other embodiments, peptide analogs comprise at least seven amino acids selected from residues 83 to 99 of human myelin basic protein in which either L-lysine at position 91, L-threonine at position 95, or L-arginine at position 97 is altered to another amino acid, and preferably in addition the N-terminal and/or C-terminal amino acids are altered in order to reduce proteolysis upon administration of the peptide analog. In a preferred aspect, the N- and/or C-terminal amino acids are of the D-form.

In other embodiments, the peptide analogs comprise at least seven amino acids selected from residues 83 to 99 of human myelin basic protein in which either L-lysine at position 91, L-threonine at position 95, or L-arginine at position 97 is altered to another amino acid and in addition up to three other amino acid alterations are made. Any residue within 83–99 may be altered except that in a peptide analog in which residue 91 is altered, residue 97 may not be altered. Likewise, in a peptide analog in which residue 97 is altered, residue 91 may not be altered.

Other embodiments provide peptide analogs comprising at least seven amino acids selected from residues 83 to 99 of human myelin basic protein in which either L-lysine at position 91, L-threonine at position 95, or L-arginine at position 97 is altered to another amino acid. In preferred aspects, residue 91, 95 or 97 are altered to either alanine or the corresponding D-amino acid.

Further aspects of the present invention provide a pharmaceutical composition comprising a peptide analog according to the embodiments set out above in which the peptide analog is contained in a physiologically acceptable carrier or diluent.

Still additional aspects of the present invention provide methods of treating multiple sclerosis by administering to a patient a therapeutically effective amount of a pharmaceutical composition comprising a peptide analog as described above in combination with a physiologically acceptable carrier, diluent and/or adjuvant.

Further aspects of the present invention provide methods for using a peptide analog as described above to induce a Th2 immune response to myelin basic protein or a peptide analog thereof in a patient. This Th2 immune response can most appropriately be described as a vaccine effect, as shown hereinafter. Such methods comprise the step of administering to a patient a therapeutically effective amount of a pharmaceutical composition comprising a peptide analog as described herein. The pharmaceutical composition is preferably a formulation that favors a Th2 type immune response. Such a composition may include an adjuvant, such as alum.

These and other aspects of the invention will become evident upon reference to the following detailed description and attached drawings. In addition, various references are set forth below which describe in more detail certain procedures or compositions. Each of these references are incorporated herein by reference in their entirety as if each were individually noted for incorporation.

BRIEF DESCRIPTION OF THE DRAWINGS

FIG. 1 depicts DNA and predicted amino acid sequence for human myelin basic protein (SEQ ID NOs:1 and 2 respectively).

FIG. 2 depicts the response of draining lymph node cells from Lewis rats immunized 9–10 days previously with MBP (87–99) to 10 μM of MBP (87–99), medium, the unrelated peptide motilin, and six different MBP analogs. A, L-alanine; k, D-lysine; t, D-threonine; r, D-arginine.

FIG. 3 is a graph displaying the proliferative response of the T cell line NBI to residue 91-substituted analogs of human myelin basic protein (87–99). Ten different substitutions were tested. The proliferative response of the rat T cell line in response to concentrations of peptide analogs ranging from 0 to 150 μM was determined. The extent of proliferation is shown as counts per minute; standard errors of the mean were less than ±10%. MOT, motilin, a peptide unrelated to MBP; MBP (87–99), human myelin basic protein residues 87–99; K, lysine; R, arginine; N, asparagine; H, histidine; L, leucine; S, serine; G, glycine; k, D-Lysine; E, glutamic acid; F, phenylalanine; A, alanine.

FIG. 4 is a graph displaying the proliferative response of the T cell line NBI to residue 95-substituted analogs of human myelin basic protein (87–99). Ten different substitutions were tested. The proliferative response of the rat T cell line in response to concentrations of peptide analogs ranging from 0 to 150 μM was determined. The extent of proliferation is shown as counts per minute; standard errors of the mean were less than ±10%. MOT, motilin, a peptide unrelated to MBP; MBP (87–99), human myelin basic protein residues 87–99; T, threonine; A, alanine; t, D-threonine; G, glycine; I, isoleucine; Y, tyrosine; Q, glutamine; S, serine; K, lysine; E, glutamic acid; H, histidine.

FIG. 5 is a graph displaying the proliferative response of the T cell line NBI to residue 97-substituted analogs of human myelin basic protein. Eleven different substitutions were tested. The proliferative response of the T cells to concentrations of peptide analogs ranging from 0 to 150 μM was determined. The extent of proliferation is displayed as counts per minute. MBP 87–99, myelin basic protein (87–99); R, arginine; a, D-alanine; r, D-arginine; G, glycine; K, lysine; Q, glutamine; E, glutamic acid; T, threonine; L, leucine; F, phenylalanine; H, histidine; A, alanine.

FIG. 6 is a graph illustrating the ability of peptide analogs of MBP to inhibit proliferation of rat T cells that are reactive to MBP. The proliferative response of draining lymph node cells from rats immunized with MBP (87–99) to 16.7, 50, or 150 μM of each analog, or 5 μM of MBP (87–99) is displayed. Analogs were added in the presence of 5 μM MBP (87–99). The extent of proliferation is shown as counts per minute. Controls consisted of MBP (87–99) only at 5 μM and medium only. h88/A91 refers to a representative peptide analog of MBP (87–99) with D-histidine at residue 88 and alanine at residue 91; h88/A91/p99 refers to another representative peptide analog of MBP (87–99) with D-histidine at 88, alanine at residue 91, and D-proline at residue 99.

FIG. 7 is a graph demonstrating the inhibition of EAE induction in Lewis rats following injection of MBP (87–99). Arrows indicate days that either PBS (control) or h88/A91 peptide analog were administered. EAE was recorded as 0, no symptoms; 1, tail paralysis; 2, hind limb weakness; 3, hind limb paralysis; 4, hind and front limb paralysis.

FIG. 8 depicts the amino acid sequence in single letter code for residues 83 to 99 of human myelin basic protein and the amino acid sequences of the peptide analogs NBI-5719 (SEQ ID NO:4), NBI-5748 (SEQ ID NO:5), NBI-5765 (SEQ ID NO:6), NBI-5788 (SEQ ID NO:7), and NBI-5789 (SEQ ID NO:8). A dash indicates amino acid identity. MBP (83–99), myelin basic protein residues 83 to 99; a, D-alanine; A, L-alanine; K, L-lysine; L, L-leucine.

FIG. 9 is a graph demonstrating the inhibition of EAE induction in Lewis rats following injection of MBP (83–99). Lewis rats were injected with MBP (83–99) at day 0. At day 9, rats were injected with either a control peptide, sperm whale myoglobin (110–121) or the peptide analog, NBI-5788 (SEQ ID NO:7). Each data point represents the average of the clinical score of six animals.

FIG. 10 is a graph demonstrating the inhibition of EAE induction in Lewis rats following injection of MBP (83–99). Lewis rats were injected with MBP (83–99) at day 0. At day 9, rats were injected with either a control peptide, sperm whale myoglobin (110–121) or the peptide analog, NBI-5788 (SEQ ID NO:7). Each data point represents the average of the clinical score of six animals.

FIG. 11 is a graph demonstrating the inhibition of EAE induction in Lewis rats following injection of MBP (83–99).

Lewis rats were injected with MBP (83–99) at day 0. At day 9, rats were injected with either a control peptide, sperm whale myoglobin (110–121) or the peptide analog, NBI-5765 (SEQ ID NO:6). Each data point represents the average of the clinical score of six animals.

FIG. 12 is a graph demonstrating the inhibition of EAE induction in SJL/J mice following injection of MBP (87–99). Groups of mice were injected intraperitoneally on a weekly basis for four weeks with either a control peptide or the peptide analog, NBI-5719 (SEQ ID NO:4) or NBI-5765 (SEQ ID NO:6). Each data point represents the average of the clinical score for ten mice.

Figure 21:
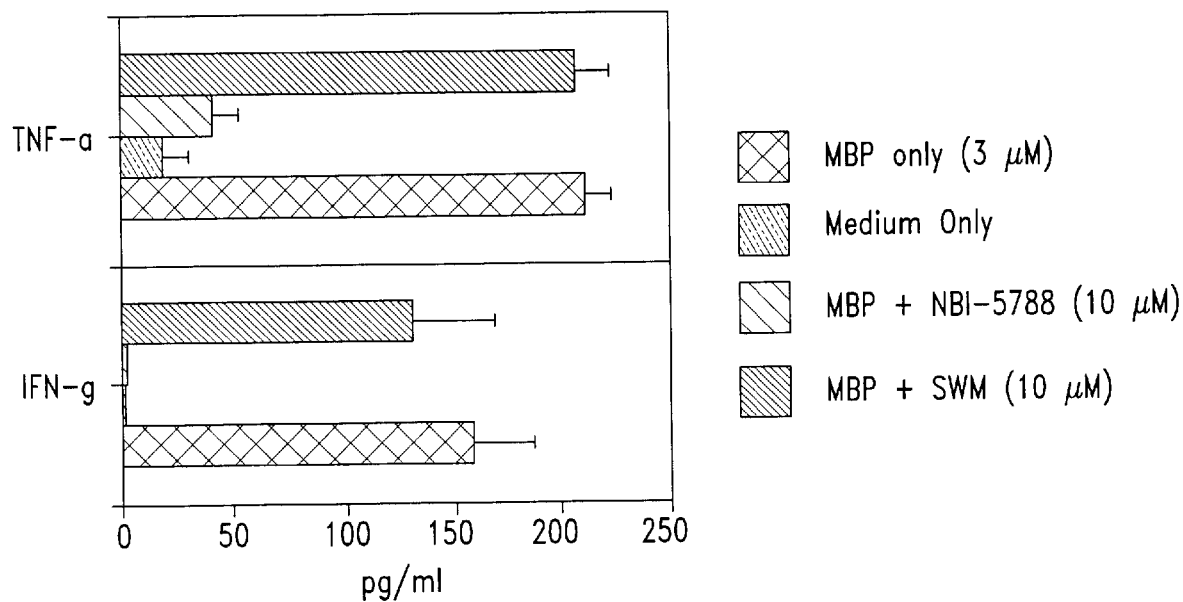

FIG. 21 is a graph displaying the production of TNF-α and IFN-γ by a Dr 2b restricted human T cell clone, 5F6, which is reactive to MBP. The T cell clone was incubated in the presence of 3 μM MBP (93–99) with either 10 μM of NBI-5788 (SEQ ID NO:7) or sperm whale myoglobin or medium only. The expression level of TNF-α and IFN-γ are displayed as pg/ml.

Figure 22:
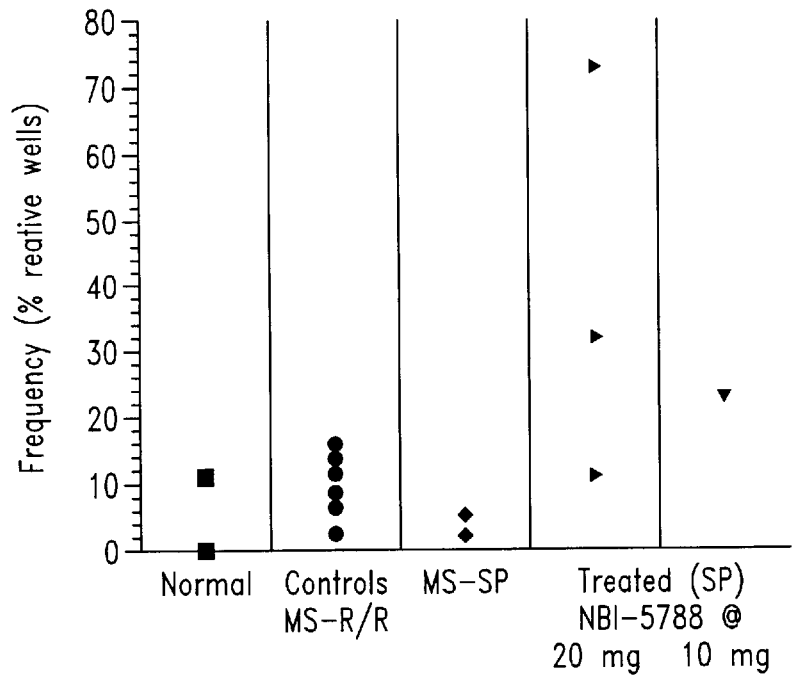

FIG. 22 is a graph depicting the frequency of peptide analog responsive cells isolated from human peripheral blood. Peripheral blood was obtained from two normal, healthy individuals (normal), from eight patients with multiple sclerosis that did not receive peptide analog (MS-relapsing remitting (R/R) and MS-secondary progressive (SP)) and from four MS patients that were treated with the peptide analog NBI-5788 (SEQ ID NO:7), either 20 mg or 10 mg as indicated one per week for four weeks. For treated patients, samples were obtained one year after administration of the peptide analog. Cells were incubated with NBI-5788 (SEQ ID NO:7), antigen presenting cells were added, and the percent of wells showing cell proliferation was measured based on thymidine incorporation.

Figure 23:
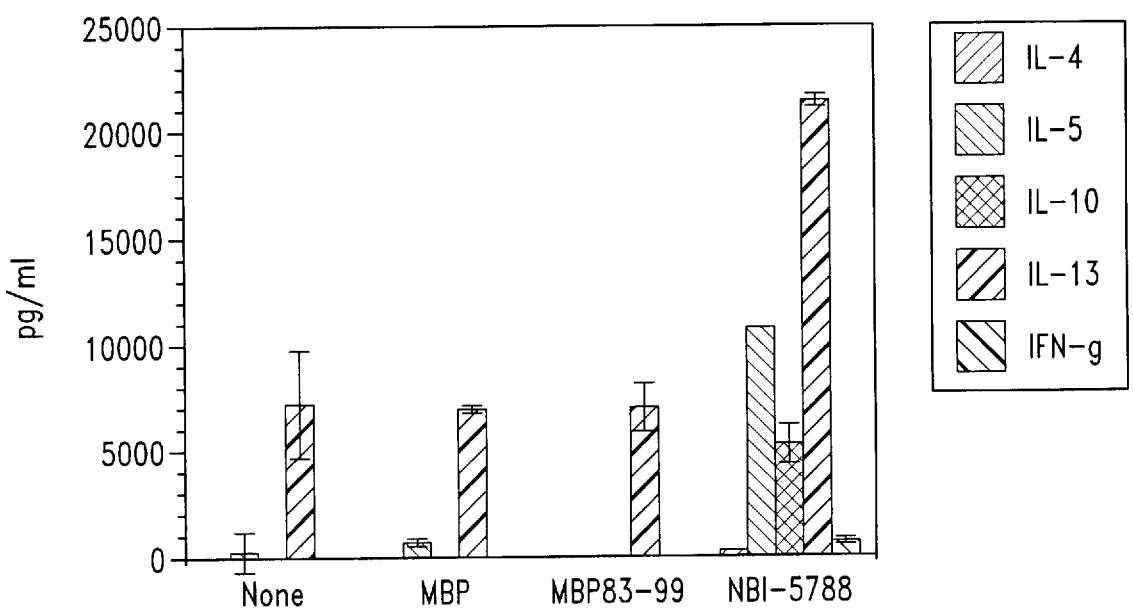

FIG. 23 is a histogram depicting the cytokine response of the T cell line LW80 which was derived from an MS patient treated with 20 mg of the peptide analog NBI-5788 (SEQ ID NO:7). Levels of IL-4, IL-5, IL-10, IL-13 and interferon-γ were assayed for cells exposed to no antigen (none), myelin basic protein (MBP), myelin basic protein peptide containing residues 83–99 (MBP83–99) and the peptide analog of residues 83–99 (NBI-5788 (SEQ ID NO:7)).

Figure 24:
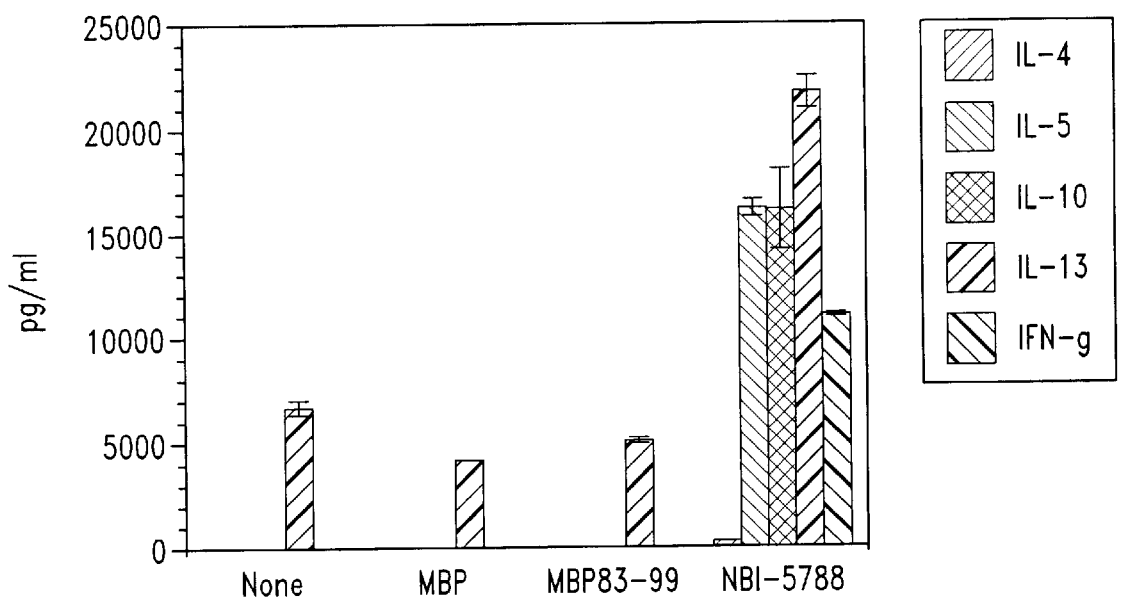

FIG. 24 is a histogram depicting the cytokine response of the T cell line LW88, which was derived from an MS patient treated with 20 mg of the peptide analog NBI-5788 (SEQ ID NO:7). Levels of IL-4, IL-5, IL-10, IL-13 and interferon-γ were assayed for cells exposed to no antigen (none), myelin basic protein (MBP), myelin basic protein peptide containing residues 83–99 (MNBP83–99) and the peptide analog of residues 83–99 (NBI-5788 (SEQ ID NO:7)).

Figure 25:
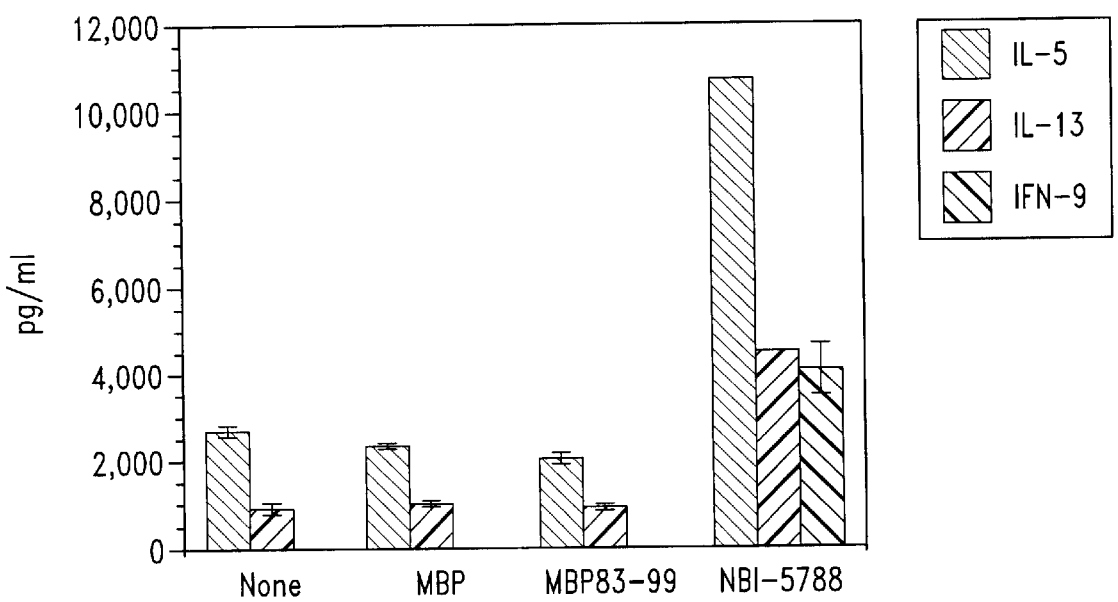

FIG. 25 is a histogram depicting the cytokine response of the T cell line LW90, which was derived from an MS patient treated with 20 mg of the peptide analog NBI-5788 (SEQ ID NO:7). Levels of IL-4, IL-5, IL-10, IL-13 and interferon-γ were assayed for cells exposed to no antigen (none), myelin basic protein (MBP), myelin basic protein peptide containing residues 83–99 (MBP83–99) and the peptide analog of residues 83–99 (NBI-5788 (SEQ ID NO:7)).

Figure 26:
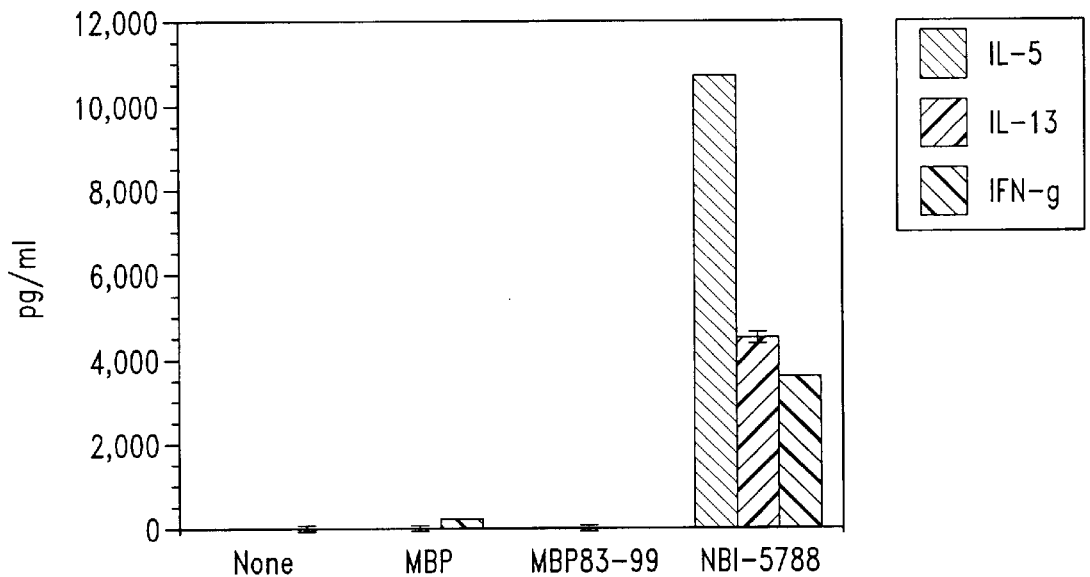

FIG. 26 is a histogram depicting the cytokine response of the T cell line LW93, which was derived from an MS patient treated with 20 mg of the peptide analog NBI-5788 (SEQ ID NO:7). Levels of IL-4, IL-5, IL-10, IL-13 and interferon-γ were assayed for cells exposed to no antigen (none), myelin basic protein (MBP), myelin basic protein peptide containing residues 83–99 (M1BP83–99) and the peptide analog of residues 83–99 (NBI-5788 (SEQ ID NO:7)).

Figure 27:
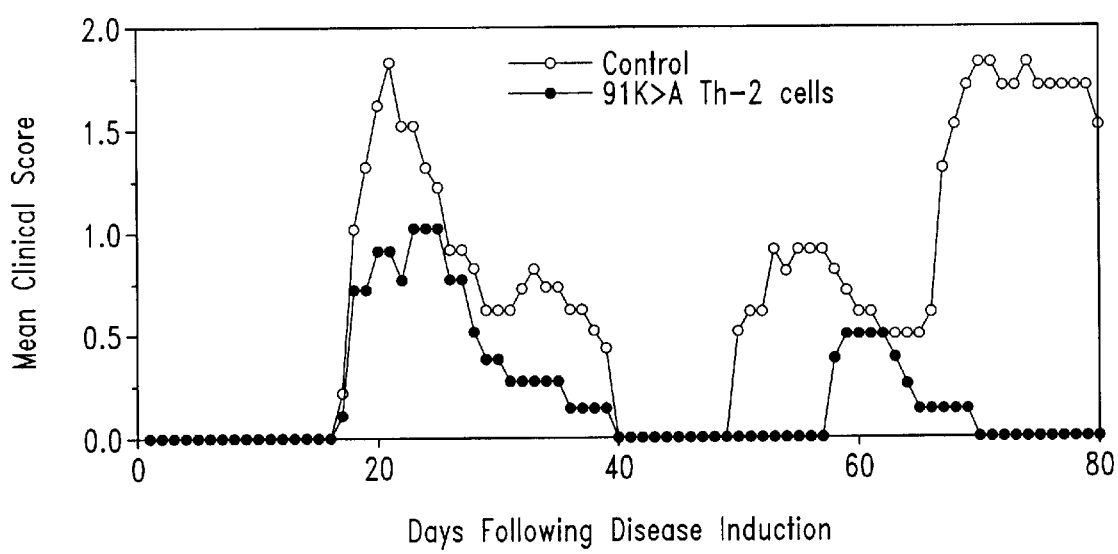

FIG. 27 is a graph showing the effect of a T cell line responsive to a peptide analog comprising residues 83–99 of MBP, in which the lysine at residue 91 is altered to an alanine, on MBP 83–99 and proteolipid (PLP 139–151) induced EAE in SJL/J mice. The effect on disease is presented as mean clinical score. Data for the analog-responsive T cell line is presented as dark circles, and data for syngeneic spleen cells is presented as open circles.

Figure 28:
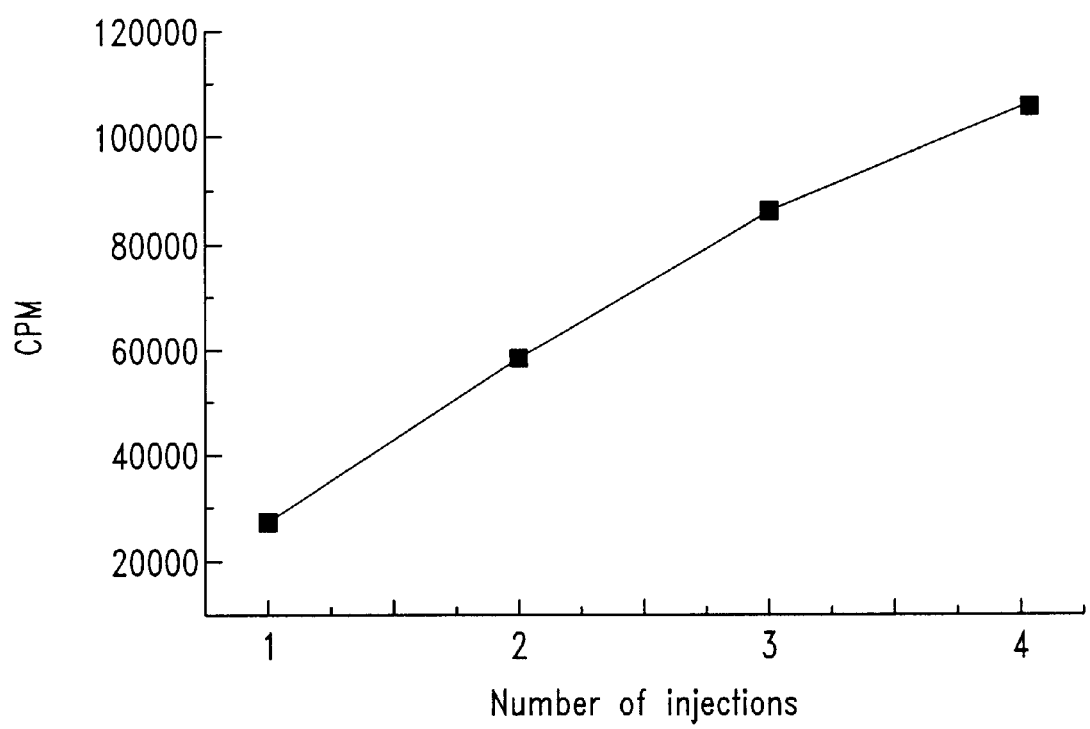

FIG. 28 is a graph depicting the effect of repeated subcutaneous injections of soluble NBI-5788 on the proliferative response of draining lymph node T cells of SJL mice.

The proliferative response is presented as cpm and the data shown represent the mean of triplicate wells.

DETAILED DESCRIPTION OF THE INVENTION

Prior to setting forth the invention, it may be helpful to an understanding thereof to set forth definitions of certain terms and abbreviations that will be used hereinafter.

"Human myelin basic protein" ("MBP") refers to a protein found in the cytoplasm of human oligodendroglial cells. The nucleotide sequence and predicted amino acid sequence of human MBP are presented in FIG. 1 (SEQ. ID Nos. 1 and 2). Although not depicted in FIG. 1, different molecular forms of human myelin basic protein generated by differential splicing or post-translational modification are also within the scope of this invention.

"Peptide analogs" of myelin basic protein are at least 7 amino acids in length and contain at least one difference in amino acid sequence between the analog and native human myelin basic protein, one of which is a difference at residue 91, 95 or 97. Unless otherwise indicated, a named amino acid refers to the L-form. An L-amino acid from the native peptide may be altered to any other one of the 20 L-amino acids commonly found in proteins, any one of the corresponding D-amino acids, rare amino acids, such as 4-hydroxyproline, and hydroxylysine, or a non-protein amino acid, such as β-alanine and homoserine. Also included within the scope of the present invention are amino acids which have been altered by chemical means such as methylation (e.g., (α-methylvaline), amidation of the C-terminal amino acid by an alkylamine such as ethylamine, ethanolamine, and ethylene diamine, and acylation or methylation of an amino acid side chain function (e.g., acylation of the epsilon amino group of lysine).

"Residue 83," "residue 84," "residue 89," "residue 91," "residue 95," and "residue 97" (also called position 83, position 89, position 91, position 95, and position 97, respectively), refer to amino acids 83, 84, 89, 91, 95, and 97 of human myelin basic protein as displayed in FIG. 1 or the amino acid at a comparative position. More specifically, the numbering system for these residues relates to the amino acid position within the native human protein, regardless of the length of the peptide or the amino acid position within that peptide.

The amino acids are referred to by their standard three-letter or one-letter code. Unless otherwise specified, the L-form of the amino acid is intended. When the 1-letter code is used, a capital letter denotes the L-form and a small letter denotes the D-form. The one letter code is as follows: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; and Y, tyrosine.

Peptide Analogs of Myelin Basic Protein

As noted above, the present invention provides peptide analogs comprising at least 7 amino acids selected from residues 83–99 of human myelin basic protein and including an alteration of the naturally occurring L-lysine at position 91, L-threonine at position 95, or L-arginine at position 97, to another amino acid. In one aspect, the peptide analog includes additional alteration of one to three L-amino acids at positions 84, 86, 87, 88, 89, 91, 95, 97, 98 and/or 99 of human myelin basic protein as long as 91 and 97 are not both altered in the same peptide analog. In another aspect, the peptide analog additionally has the N-terminal and/or C-terminal residues altered to an amino acid such that proteolysis is reduced upon administration to a patient compared to a peptide analog without these additional alterations. In a further aspect, the peptide analog of MNBP comprises at least seven amino acids selected from residues 83–99 and has one of the residues at position 91, 95 or 97 altered to an amino acid not present in native MBP protein. In addition to such single alterations, one to three additional alterations of residues 83 to 99 may be made, as long as residues 91 and 97 are not altered in the same peptide analog. In yet a further aspect, the peptide analog of MNBP comprises residues 83 to 99, the L-lysine at position 91 is altered to another amino acid and two to four additional amino acids selected from residues 83 to 90 and 92 to 99 are altered to another amino acid. Preferably, at least one amino acid is substituted with a charged amino acid. In addition, the N-terminal and/or C-terminal amino acids may be altered to a D-amino acid.

The peptide analogs are preferably 7 to 17 amino acids, and usually not longer than 20 amino acids. Particularly preferred peptide analogs are 14 to 17 amino acids in length. Residues 83, 89, 91, 95, and 97, which are L-glutamic acid, L-phenylalanine, L-lysine, L-threonine, and L-arginine, respectively, in the native human protein, are the key residues. Within the subject invention, analogs must have an amino acid other than L-lysine at position 91, an amino acid other than L-threonine at position 95, or an amino acid other than L-arginine at position 97.

As noted above, any amino acid alteration at position 91 is within the scope of this invention. Preferred peptide analogs include alteration of L-lysine to any one of the following amino acids: D-lysine, alanine, glycine, glutamic acid, phenylalanine, arginine, asparagine, histidine, leucine or serine. These amino acids include both conservative (similar charge, polarity, hydrophobicity, and bulkiness) and non-conservative amino acids. Although typically one might expect that only non-conservative amino acid alterations would provide a therapeutic effect, unexpectedly even conservative changes (e.g., arginine) greatly affect the function of the peptide analog as compared to the native peptide. Such diversity of substitution is further illustrated by the fact that the preferred amino acids noted above are hydrophobic and hydrophilic, charged and uncharged, polar and non-polar.

In addition, any amino acid substitution at residue 95 is also within the scope of this invention. Preferred peptide analogs contain alterations of L-threonine to any one of the following amino acids: D-threonine, alanine, glycine, isoleucine, tyrosine, glutamine, serine, lysine, glutamic acid and histidine. Other preferred alterations are to non-conservative amino acids. Particularly preferred alterations are to alanine or D-threonine.

Similarly, any amino acid alteration at position 97 is within the scope of this invention. Preferred peptide analogs include alteration of L-arginine to D-alanine, D-arginine, glycine, lysine, glutamine, glutamic acid, threonine, leucine, phenylalanine, histidine or alanine. Other preferred alterations are to non-conservative amino acids. Particularly preferred alterations are to alanine and D-arginine.

Further, any amino acid at position 83 and position 89 are within the scope of this invention. Preferred peptide analogs contain alterations of L-glutamic acid at residue 83 to any one of the following amino acids: D-alanine, L-alanine, D-glutamic acid and L-phenylalanine at position 89 to alanine, leucine, valine, isoleucine.

In addition, in certain embodiments at least one other amino acid selected from residues 84, 86, 87, 88, 89, 95, 98, or 99 is altered. In such embodiments, if two other amino acids are changed, one is preferably selected from residues 86, 87, 88, or 89, and the other is selected from residues 98 or 99. Alternatively, up to three alterations at any positions may be made. In other embodiments, at least two to four amino acids (in addition to position 91) are altered. In such embodiments, the altered amino acids are preferably selected from positions 83, 84, 89 and 98.

With these general considerations in mind, peptide analogs within the scope of the invention have an alteration of residue 91, residue 95, or of residue 97. One set of preferred peptide analogs have double alterations. In one embodiment, residue 91 is altered as noted above, residue 87 is altered to D-valine, residue 88 to D-histidine or residue 99 to D-proline. Similarly, in another embodiment, residue 97 is altered as noted above, and either residue 87 is altered to D-valine, residue 88 to D-histidine or residue 99 to D-proline. In yet another embodiment, residue 95 is altered as noted above and residue 87 is altered to D-valine, residue 88 to D-histidine or residue 99 to D-proline.

A second set of preferred peptide analogs contains analogs having three substitutions. In one embodiment, residue 91 is altered to alanine, residue 87 is altered to D-valine or residue 88 is altered to D-histidine and residue 99 is altered to D-proline. In another embodiment, residue 97 is altered to alanine, residue 88 is altered to D-histidine and residue 99 to D-proline. In yet another embodiment, residue 95 is altered to alanine, residue 88 is altered to D-histidine and residue 99 to D-proline. In still another embodiment, residue 83 is altered to D-alanine, residue 89 is altered to alanine, and residue 91 is altered to alanine.

A third set of preferred peptide analogs contains analogs having four substitutions. In one embodiment, residue 83 is altered to D-alanine, residue 84 is altered to lysine, residue 89 is altered to leucine and residue 91 is altered to alanine. In another embodiment, residue 83 is altered to D-alanine, residue 84 is altered to lysine, and residues 89 and 91 are altered to alanine.

A fourth set of preferred peptide analogs have five substitutions. In one embodiment, residues 83 and 98 are altered to D-alanine, residue 84 is altered to lysine, and residues 89 and 91 are altered to alanine. In another embodiment, residues 83 and 98 are altered to D-alanine, residue 84 is altered to lysine, residue 89 is altered to leucine and residue 91 is altered to alanine.

Peptide analogs may be synthesized by standard chemistry techniques, including synthesis by automated procedure. In general, peptide analogs are prepared by solid-phase peptide synthesis methodology which involves coupling each protected amino acid residue to a resin support preferably a 4-methyl-benzhydrylamine resin, by activation with dicyclohexylcarbodimide to yield a peptide with a C-terminal amide. Alternatively, a chloromethyl resin (Merrifield resin) may be used to yield a peptide with a free carboxylic acid at the C-terminus. Side-chain functional groups are protected as follows: benzyl for serine, threonine, glutamic acid, and aspartic acid; tosyl for histidine and arginine; 2-chlorobenzyloxycarbonyl for lysine and 2,6-dichlorobenzyl for tyrosine. Following coupling, the t-butyloxycarbonyl protecting group on the alpha amino function of the added amino acid is removed by treatment with trifluoroacetic acid followed by neutralization with di-isopropyl-ethylamine. The next protected residue is then coupled onto the free amino group, propagating the peptide chain. After the last residue has been attached, the protected peptide-resin is treated with hydrogen fluoride to cleave the peptide from the resin, as well as deprotect the side chain functional groups. Crude product can be further purified by gel filtration, HPLC, partition chromatography, or ion-exchange chromatography.

Peptide analogs within the present invention should (a) compete for the binding of native MBP peptide (e.g., 87–99 in rats; 83–99 in humans) to MHC; (b) not cause proliferation of an MBP (87–99)-reactive T cell line; and (c) inhibit induction of experimental allergic encephalomyelitis (EAE) by MBP (87–99) in rodents.

Thus, candidate peptide analogs may be screened for their ability to treat MS by (1) an assay measuring competitive binding to MHC, (2) an assay measuring a T cell proliferation, and (3) an assay assessing induction/inhibition of EAE. Those analogs that inhibit binding of the native peptides, do not stimulate proliferation of MBP-reactive cell lines, and inhibit the development of EAE by native human MBP (87–99), are useful therapeutics. Although not essential, a further safety assay may be performed to demonstrate that the analog does not itself induce EAE.

Binding of peptides to MHC molecules may be assayed on whole cells. Briefly, Lewis rat spleen cells are cultured for 3 hours to allow adherent cells to stick to polystyrene petri dishes. Non-adherent cells are removed. Adherent cells, which contain cells expressing MHC class II molecules, are collected by scraping the dishes. The binding of peptide analogs to cells is measured by a fluorescence assay. In this assay, splenic adherent cells are mixed with different concentrations of peptide analogs and incubated for 1 hour at 37° in a $CO_2$ incubator. Following incubation, biotin-labeled MBP (87–99) is added to the culture wells. The cells are incubated for another hour and then washed three times in medium. Phycoerythrin-conjugated or fluorescein-conjugated streptavidin is added along with a fluorochrome-labeled OX-6 or OX-17 monoclonal antibody, which reacts with rat MHC Class 11 I-A and I-E, respectively. The cells are washed twice before analysis by flow cytometry. Fluorescence intensity is calculated by subtracting the fluorescence value obtained from cells stained with phycoerythrin-streptavidin alone (control staining) from the fluorescence value obtained from biotin-labeled MBP native peptide plus phycoerythrin-streptavidin (experimental staining). Staining without analog establishes a 100% value. Percent inhibition is calculated for each analog and expressed as $IC_{50}$ values. A peptide analog with an $IC_{50}$ value of less than 100 μM is suitable for further screenings.

Candidate peptide analogs are further tested for their property of causing or inhibiting proliferation of T cell lines. Two different assays may be used as alternatives. The first measures the ability of the analog to cause proliferation of T cells in a direct fashion. The second measures the ability of the peptide analog to inhibit proliferation of T cells induced by native MBP peptide.

In the direct proliferation assay, MBP (87–99) reactive T cell lines may be used as target cells. T cell lines are established from lymph nodes taken from rats injected with MBP (87–99). Lymph node cells are isolated and cultured for 5 to 8 days with MBP (87–99) and IL-2 as a source of T cell growth factors. Viable cells are recovered and a second round of stimulation is performed with MBP (87–99 or 83–99) and irradiated splenocytes as a source of growth factors. After 5 to 6 passages in this manner, the proliferative potential of the cell lines are determined. MBP-reactive lines are used in the proliferation assay. In this assay, T cell lines are cultured for three days with various concentrations of peptide analogs and irradiated, autologous splenocytes. After three days, 0.5–1.0 µCi of [$^3$H]-thymidine is added for 12–16 hours. Cultures are harvested and incorporated counts determined. Mean CPM and standard error of the mean are calculated from triplicate cultures.

As an alternative to the use of T cell lines described above, draining lymph node cells from Lewis rats injected with MBP (87–99) may be used. Preferably, this assay is used in combination with the proliferation assay using T cell lines. Briefly, Lewis rats are injected subcutaneously with MBP (87–99) peptide in complete Freund's adjuvant. Nine to ten days later, draining lymph node cells are isolated and single-cell suspensions are prepared. Lymph node cells are incubated with various concentrations of peptide analogs for three days in a humidified air chamber containing 6.5% $CO_2$. After incubation, the cultures are pulsed with 1–2 µCi of [$^3$H]-thymidine for 12–18 hours. Cultures are harvested on fiberglass filters and counted in a scintillation counter. Mean CPM and the standard error of the mean are calculated from data determined in triplicate cultures. Peptide analogs yielding results that are more than three standard deviations below the mean response from a comparable concentration of MBP (87–99) are considered non-stimulatory. Peptide analogs which do not stimulate proliferation at concentrations of less than or equal to 50 µM are suitable for further screenings.

The second or alternative assay is a competition assay for T cell proliferation. In this assay, antigen presenting spleen cells are first irradiated and then incubated with native MBP (87–99) peptide for 2–4 hours. These cells are then washed and further cultured with T cells reactive to MBP (87–99). Various concentrations of candidate peptide analogs are included in cultures for an additional 3 days. Following this incubation period, each culture is pulsed with 1 µCi of [$^3$H]-thymidine for an additional 12–18 hours. Cultures are then harvested on fiberglass filters and counted as above. Mean CPM and standard error of the mean are calculated from data determined in triplicate cultures. Peptide analogs which inhibit proliferation to approximately 25% at a concentration of 50 µM or greater are suitable for further screening.

Human T cells reactive to M13P (83–99) may alternatively be used to measure the ability of the peptide analog to inhibit proliferation of T cells induced by native MBP (83–99) peptide. MBP-specific T cells may be obtained as previously described by Martin et al., *J. Immunol.* 148:1359–1366, 1992. Briefly, T cell lines are established by culture of human T cells with irradiated, DR-matched peripheral blood cells in MEM supplemented with 2 mM L-glutamine, 50 µg/ml gentamicin, penicillin and streptomycin, 100 U/ml rIL-2, and 10% human AB negative serum. Proliferation of these T cell lines is stimulated by culturing a clone with varying concentration (1.1–30 µM) of native MBP (89–99) peptide, 50 µM of the peptide analog or SWM peptide, in the presence of irradiated, DR matched peripheral blood cells, following incubation for approximately 60 hours, the cells are pulsed with $^3$H-thymidine for 12 hours and harvested. The amount of incorporated $^3$H-thymidine is measured.

As discussed in detail below, the production of cytokines may also be assessed. In particular, TNF-α and IFN-γ production are especially interesting. These pro-inflammatory cytokines are thought to play a role in the pathogenesis of the disease. Briefly, T cell clone is incubated in the presence of stimulating MBP peptide and peptide analog or control peptide (SWM) or medium only. After a 24 hour incubation, the levels of TNF-α and IFN-γ in the supernatant are determined using commercially available EIA kits (Endogen, Cambridge, Mass.).

Candidate peptides that compete for binding of MBP (87–99) to MHC and do not cause direct proliferation of T cell line or can inhibit proliferation by MBP (87–99), are further tested for their ability to inhibit the induction of EAE by MBP (87–99). Briefly, 500 µg of MBP (87–99) is injected as an emulsion in complete Freund's adjuvant supplemented with heat killed *Mycobacterium tuberculosis* (H37Ra). Rats are injected subcutaneously at the base of the tail with 200 µl of the emulsion. Rats are divided into two groups. Approximately 2 days prior to disease induction (usually 10 days following injection of MBP (87–99)) rats are injected intraperitoneally either with PBS or peptide analogs in PBS. Animals are monitored for clinical signs on a daily basis by an observer blind to the treatment protocol. EAE is scored on a scale of 0–4: 0, clinically normal; 1, flaccid tail paralysis; 2, hind limb weakness; 3, hind limb paralysis; 4, front and hind limbs affected. Peptide analogs injected at about 12 mg/kg or less (approximately 1 mg per rat) are considered to inhibit the development of EAE if there is a 50% reduction in the mean cumulative score over seven days following onset of disease symptoms in the control group.

In addition, as a safety measure, but not essential to this invention, suitable peptide analogs may be tested for direct induction of EAE. As described in detail in Example 2, various amounts of peptide analogs are injected at the base of the tail of rats, and the rats examined daily for signs of EAE. A peptide analog which is not considered to cause EAE has a mean cumulative score of less than or equal to 1 over seven days when about 12 mg/kg or less in complete Freund's adjuvant is injected.

Treatment and Prevention of Multiple Sclerosis

As noted above, the present invention provides methods for treating and preventing multiple sclerosis by administering to the patient a therapeutically effective amount of a peptide analog of human myelin basic protein as described herein. Patients suitable for such treatment may be identified by criteria establishing a diagnosis of clinically definite MS as defined by the workshop on the diagnosis of MS (Poser et al., *Ann. Neurol* 13:227, 1983). Briefly, an individual with clinically definite MS has had two attacks and clinical evidence of either two lesions or clinical evidence of one lesion and paraclinical evidence of another, separate lesion. Definite MS may also be diagnosed by evidence of two attacks and oligoclonal bands of IgG in cerebrospinal fluid or by combination of an attack, clinical evidence of two lesions and oligoclonal band of IgG in cerebrospinal fluid. Slightly lower criteria are used for a diagnosis of clinically probable MS.

Effective treatment of multiple sclerosis may be examined in several different ways. Satisfying any of the following criteria evidences effective treatment. Three main criteria are used: EDSS (extended disability status scale), appearance of exacerbations or MRI (magnetic resonance imaging).

The EDSS is a means to grade clinical impairment due to MS (Kurtzke, *Neurology* 33:1444, 1983). Eight functional systems are evaluated for the type and severity of neurologic impairment. Briefly, prior to treatment, patients are evaluated for impairment in the following systems: pyramidal, cerebella, brainstem, sensory, bowel and bladder, visual, cerebral, and other. Follow-ups are conducted at defined intervals. The scale ranges from 0 (normal) to 10 (death due to MS). A decrease of one full step defines an effective treatment in the context of the present invention (Kurtzke, *Ann. Neurol.* 36:573–79, 1994).

Exacerbations are defined as the appearance of a new symptom that is attributable to MS and accompanied by an appropriate new neurologic abnormality (IFNB MS Study Group, supra). In addition, the exacerbation must last at least 24 hours and be preceded by stability or improvement for at least 30 days. Briefly, patients are given a standard neurological examination by clinicians. Exacerbations are either mild, moderate, or severe according to changes in a Neurological Rating Scale (Sipe et al., Neurology 34:1368, 1984). An annual exacerbation rate and proportion of exacerbation-free patients are determined. Therapy is deemed to be effective if there is a statistically significant difference in the rate or proportion of exacerbation-free patients between the treated group and the placebo group for either of these measurements. In addition, time to first exacerbation and exacerbation duration and severity may also be measured. A measure of effectiveness as therapy in this regard is a statistically significant difference in the time to first exacerbation or duration and severity in the treated group compared to control group.

MRI can be used to measure active lesions using gadolinium-DTPA-enhanced imaging (McDonald et al. *Ann. Neurol* 36:14, 1994) or the location and extent of lesions using $T_2$-weighted techniques. Briefly, baseline MRIs are obtained. The same imaging plane and patient position are used for each subsequent study. Positioning and imaging sequences are chosen to maximize lesion detection and facilitate lesion tracing. The same positioning and imaging sequences are used on subsequent studies. The presence, location and extent of MS lesions are determined by radiologists. Areas of lesions are outlined and summed slice by slice for total lesion area. Three analyses may be done: evidence of new lesions, rate of appearance of active lesions, percentage change in lesion area (Paty et al., *Neurology* 43:665, 1993). Improvement due to therapy is established when there is a statistically significant improvement in an individual patient compared to baseline or in a treated group versus a placebo group.

Candidate patients for prevention may be identified by the presence of genetic factors. For example, a majority of MS patients have HLA-type DR2a and DR2b. The MS patients having genetic dispositions to MS who are suitable for treatment fall within two groups. First are patients with early disease of the relapsing remitting type. Entry criteria would include disease duration of more than one year, EDSS score of 1.0 to 3.5, exacerbation rate of more than 0.5 per year, and free of clinical exacerbations for 2 months prior to study. The second group would include people with disease progression greater than 1.0 EDSS unit/year over the past two years.

Efficacy of the peptide analog in the context of prevention is judged based on the following criteria: frequency of MBP reactive T cells determined by limiting dilution, proliferation response of MBP reactive T cell lines and clones, cytokine profiles of T cell lines and clones to MBP established from patients. Efficacy is established by decrease in frequency of reactive cells, a reduction in thymidine incorporation with altered peptide compared to native, and a reduction in TNF-$\alpha$ and IFN-$\gamma$. Clinical measurements include the relapse rate in one and two year intervals, and a change in EDSS, including time to progression from baseline of 1.0 unit on the EDSS which persists for six months. On a Kaplan-Meier curve, a delay in sustained progression of disability shows efficacy. Other criteria include a change in area and volume of T2 images on MRI, and the number and volume of lesions determined by gadolinium enhanced images.

Peptide analogs of the present invention may be administered either alone, or as a pharmaceutical composition. Briefly, pharmaceutical compositions of the present invention may comprise one or more of the peptide analogs described herein, in combination with one or more pharmaceutically or physiologically acceptable carriers, diluents or excipients. Such compositions may comprise buffers such as neutral buffered saline, phosphate buffered saline and the like, carbohydrates such as glucose, mannose, sucrose or dextrans, mannitol, proteins, polypeptides or amino acids such as glycine, antioxidants, chelating agents such as EDTA or glutathione, adjuvants (e.g., aluminum hydroxide) and preservatives. In addition, pharmaceutical compositions of the present invention may also contain one or more additional active ingredients, such as, for example, cytokines like $\beta$-interferon.

Compositions of the present invention may be formulated for the manner of administration indicated, including for example, for oral, nasal, venous, intracranial, intraperitoneal, subcutaneous, or intramuscular administration. Within other embodiments of the invention, the compositions described herein may be administered as part of a sustained release implant. Within yet other embodiments, compositions of the present invention may be formulated as a lyophilizate, utilizing appropriate excipients which provide stability as a lyophilizate, and subsequent to rehydration.

Pharmaceutical compositions of the present invention may be administered in a manner appropriate to the disease to be treated (or prevented). The quantity and frequency of administration will be determined by such factors as the condition of the patient, and the type and severity of the patient's disease. Within particularly preferred embodiments of the invention, the peptide analog or pharmaceutical compositions described herein may be administered at a dosage ranging from 5 to 50 mg/kg, although appropriate dosages may be determined by clinical trials. Patients may be monitored for therapeutic effectiveness by MRI, EDSS, and signs of clinical exacerbation, as described above.

It has been found, within the context of the present invention, that peptide analogs as described herein generally shift the T cell response away from Th1- to Th2-cytokine secretion. Peptide analogs generally antagonize the proliferative and Th1-like cytokine responses of certain human T cells specific for MBP(83–99). Peptide analogs further induce a protective analog-specific cellular immune response that is primarily Th2-like in nature. Such T cells may mediate bystander suppression of autoreactive T cells to various antigenic determinants of myelin when myelin is damaged. Accordingly, such analogs may be used to induce a Th2 immune response to myelin basic protein or an analog thereof in a patient. In general, an analog is said to induce a Th2 immune response in a patient if administration of the analog to a patient as described herein results in the production of analog-specific T cells that produce one or more Th2-type cytokines (e.g., IL-4, IL-5, IL-10 and/or IL-13) at a level that is statistically greater than that observed for T cells from the patient prior to administration of the analog. T cells may be obtained from a patient and assayed for specific cytokines using well known techniques, and as described herein. Within such methods, the pharmaceutical composition is preferably a formulation that favors a Th2 type immune response. For example, any of a variety of adjuvants that favor such an immune response may be employed. Suitable adjuvants include alum (aluminum hydroxide).

It has further been found, within the context of the present invention, that the peptide analogs provided herein can be used to induce a persistent systemic immune response to myelin basic protein or a peptide analog thereof. A "persistent systemic immune response" as used herein is an immune response that is detectable in peripheral blood derived lymphocytes, using methods provided herein, for at least one week, preferably for 1 to 12 months following administration of a peptide analog. Such methods comprise administering to a patient a therapeutically effective amount of a peptide analog as provided herein. One preferred peptide analog is NBI-5788 (SEQ ID NO:7), also referred to as CGP 77116. To induce a systemic immune response, a peptide analog as recited herein is preferably administered in an amount ranging from 0.1 to 100 mg/patient (e.g., 1, 3, 10 or 50 mg/patient), once a week for four weeks. As will be apparent to one skilled in the art, the foregoing amounts can also be administered for periods of time longer than 4 weeks, such as for 12 weeks. In order to maintain the systemic immune response, dosing may be continued at intervals ranging from one week to 6 months.

The following examples are offered by way of illustration and not by way of limitation.

EXAMPLE 1

Preparation of Peptides

The peptides were synthesized by solid phase methodology on a peptide synthesizer (Beckman model 990). Peptides with an amidated carboxyl-terminus were prepared with a p-methylbenzhydrylamine resin (MBHA resin); for peptides with a free carboxyl-terminus, a Merrifield resin coupled with the appropriately protected amino acid was used. Both resins were obtained from Bachem Fine Chemicals (Torrance, Calif.). Derivatized amino acids (Bachem Fine Chemicals) used in the synthesis were of the L-configuration unless specified otherwise, and the N-alpha-amino function protected exclusively with the t-butyloxycarbonyl group. Side-chain functional groups were protected as follows: benzyl for serine, threonine, glutamic acid, and aspartic acid; tosyl for histidine and arginine; 2-chlorobenzyloxycarbonyl for lysine and 2,6-dichlorobenzyl for tyrosine. Coupling of the carboxyl-terminal amino acid to the MBHA resin was carried out with dicyclohexylcarbodiimide and the subsequent amino acids were coupled with dicyclohexylcarbodiimide according to Ling et al. (*Proc. Natl. Acad. Sci. USA* 81:4302, 1984). After the last amino acid was incorporated, the t-butyoxycarbonyl protecting group was removed and the peptide-resin conjugate treated with a mixture of 14 ml hydrofluoric acid (HF), 1.4 ml anisole, and 0.28 ml methylethyl sulfide per gram of resin conjugate at −20° C. for 0.5 hr and at 0° C. for 0.5 hr. HF was removed in vacuum at 0° C., and the resulting peptide and resin mixture was washed twice with diethyl ether and twice with chloroform and diethyl ether alternately. The peptide was extracted five times with 2 M acetic acid, and the extract lyophilized. The lyophilized product was first purified on a column of Sephadex G-25 fine (Pharmacia-LKB, Piscataway, N.J.) developed in 30% acetic acid to remove the truncated fragments and inorganic salts (Ling et al., 1984). Next, peptides were further purified by CM-32 carboxymethylcellulose cation-exchange chromatography (Ling et al., 1984). Final purification was achieved by partition chromatography on Sephadex G-25 fine (Ling et al., 1984). The synthetic product was characterized by amino acid analysis, mass spectrometric analysis, and reversed-phase HPLC.

EXAMPLE 2

Immunizations and EAE induction

MBP peptide and peptide analogs were dissolved in phosphate-buffered saline (PBS) and emulsified with an equal volume of incomplete Freund's adjuvant supplemented with 4 mg/ml heat-killed *Mycobacterium tuberculosis* H37Ra in oil (Difco Laboratories, Inc., Detroit, Mich.). Rats were immunized subcutaneously at the base of the tail with 0.1–0.2 ml containing 500 μg of peptide in the emulsion and were monitored for clinical signs daily. EAE was scored on a scale of 0–4, as follows: 0, clinically normal; 1, flaccid tail; 2, hind limb weakness; 3, hind limb paralysis; 4, front and hind limbs affected.

EXAMPLE 3

Long-term T cell lines

Antigen specific long-term T cell lines were derived using the method developed by Ben-Nun et al. (*Eur. J. Immunol.* 11:195, 1981). Lewis rats were injected with MBP (87–99) or MBP (83–99) as described above. Nine to ten days later draining lymph node cells were cultured ($10^7$/ml) for 5–8 days in stimulation medium (Dulbecco's modified Eagle's medium supplemented with $5\times10^{-5}$M 2-mercaptoethanol, 2 mM L-glutamine, 1 mM sodium pyruvate, 100 μg/ml penicillin, 100 μg/ml streptomycin and 10% fetal bovine serum (Hyclone Laboratories, Logan, Utah)) together with 10–20 μM of the MBP (87–99) peptide and 15 U/ml IL-2. After 5 to 8 days of culture, viable cells were collected from the interface after Ficoll-Hypaque separation and washed three times. These cells were recultured at $1\times10^7$ cells/ml in medium with $5\times10^5$ irradiated (3000 rad) autologous splenocytes as accessory cells and 10–20 μM of MBP (87–99). After 5 to 6 stimulation cycles, plates were screened by the ability of cells to proliferate in response to MBP (87–99). Positive lines were transferred to 24-well flat bottom plates and restimulated.

EXAMPLE 4

MHC binding assay

The ability of MBP peptides and peptide analogs to bind NHC was measured. An assay which characterizes the binding of peptides to ARC molecules on antigen presenting cells (APC) was employed (Mozes et al., *EMBO. J.* 8:4049, 1989; Gautam et al., *PNAS* 91:767, 1994). Spleen cells were cultured in Dulbecco's modified Eagle's medium supplemented with 10% fetal bovine serum (Hyclone Laboratories, Logan, Utah) in standard polystyrene petri dishes (100×15 mm) in a 37° C. incubator containing 6.5% $CO_2$ for 3 hours. Thereafter, non-adherent cells were removed, and the plates were washed three times with PBS. Adherent cells were collected using a cell scraper. The binding of MBP (87–99) analogs was measured using a fluorescence assay. Briefly, $5\times10^5$ splenic adherent cells in staining buffer (PBS containing 0.1% bovine serum albumin) were mixed with different concentrations ranging from 0–400 μM of MBP analogs in individual wells of U-shape 96-well microculture plates and incubated for 1 hr at 37° C. in a 6.5% $CO_2$ incubator. Following incubation, 10 μM of biotin-labeled MBP native peptide was added to culture wells for 1 h. Cells were washed three times with the staining buffer. Phycoerythrin-conjugated or fluorescein-conjugated streptavidin (Becton Dickinson, San Jose, Calif.) was added as a second step reagent (1 μg/well) along with 1 μg/well of fluorochrome-labeled OX-6 or OX-17 monoclonal antibody (Pharmingen, San Diego, Calif), which reacts with rat MHC class II I-A or I-E, respectively. The cells were washed twice before cytofluorographic analysis on a FACScan (Becton Dickinson). Fluorescence intensity for each sample was calculated by subtracting the fluorescence obtained from OX positive cells stained with phycoerythrin-streptavidin alone (control staining) from the fluorescence obtained from OX positive cells stained with biotin-labeled MBP plus phycoerythrin-streptavidin. Percent inhibition was calculated for each analog and expressed as $IC_{50}$ values.

The peptide analog, h88/A91, which contains D-histidine at position 88 and alanine at position 91 competed as effectively as MBP (87–99) for MHC against MBP (87–99). At 200 μM, MBP (87–99) inhibited binding by 68.4% and h88/A91 inhibited binding by 67.64%. At 100 μM, MBP (87–89) inhibited binding by 40% and a83, A89, A91 inhibited binding by 25%.

EXAMPLE 5

Antigen-specific lymph node cell proliferation assay

Female Lewis rats, approximately six weeks old, were purchased from Harlan Sprague, Indianapolis, Ind. MBP peptides were dissolved in phosphate-buffered saline (PBS) and emulsified with an equal volume of complete Freund's adjuvant (Difco Laboratories, Inc., Detroit, Mich.) supplemented with 2 mg/ml of heat-killed *Mycobacterium tuberculosis* H37Ra in oil (Difco). Rats were immunized subcutaneously in the base of the tail with 0.1 ml containing 100 μg of the peptide in the emulsion. Nine to ten days following immunization, rats were sacrificed, their draining lymph node removed and a single cell suspension made. Cells were resuspended to $5 \times 10^6$ cells per ml in stimulation medium containing Dulbecco's modified Eagle's medium (Gibco BRL, Gaithersburg, Md.) supplemented with 2 mercaptoethanol ($5 \times 10^{-5}$ M), L-glutamine (2 mM), sodium pyruvate (1 mM), penicillin (100 μg/ml), streptomycin (100 μg/ml), and 1% normal rat serum.

For the assay, 100 μl of the lymph node cell suspension was added to 96-well flat-bottom wells in the presence of an equal volume of medium containing 10 μM of various peptides (including: motilin as a negative control; MBP87–99; medium only or alanine or D-amino acid substituted at position 91, 95, or 97). Cultures were then incubated at 37° C. in humidified air containing 7.5% $CO_2$. After 3 days of incubation, 1.0 μCi of tritiated thymidine (20 Ci/mM; New England Nuclear) was added to each well and the plates reincubated for an additional 12–16 hours. The plates were then harvested with a Matrix filtermate harvester (Packard) and counted using an Automatic Direct Beta Counter (Packard). Mean cpm and the standard error of the mean were calculated from triplicate wells.

Figure 2:
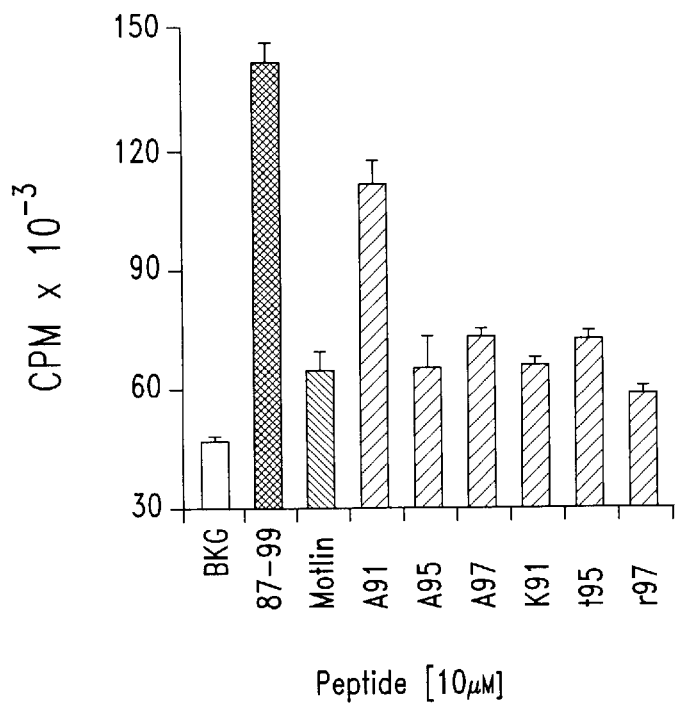

As seen in FIG. 2, MNBP (87–99) stimulated lymph node cells in contrast to the peptide analogs. Alanine alterations at positions 95 and 97 and D-amino acid alterations at residues 91, 95, and 97 failed to stimulate cells above the control peptide, motilin.

EXAMPLE 6

Antigen-specific T cell line proliferation assays

Assays for the antigen-specific proliferation assay of T cell lines were performed in 96-well flat bottom microtiter plates as described (Zamvil et al., *Nature* 317:355–358, 1985; Offner et al., *J. Immunol.* 148:1706–1711, 1992; Gold et al., *J. Immunol.* 148:1712–1717, 1992; Karin et al., *J. Exp. Med.* 180:2227–2237, 1994). T cell lines were established as described in Example 3. An initial 1:10 dilution of a 1.5 mM stock solution of MBP or the peptide analogs were added into tissue culture medium. The samples were diluted by three-fold serial dilutions (final volume 100 μl). The responding continuous T cell lines were resuspended to $4 \times 10^5$ cells per ml and 50 μl aliquots added to each well ($5 \times 10^4$ cells per well). Approximately $1 \times 10^6$ irradiated (3000R) splenocyte feeder cells were also added to each well. Cultures were then incubated at 37° C. in humidified air containing 7.5% $CO_2$ for 3 days. Twelve to sixteen hours prior to harvesting, 0.5–1.0 μCi of [$^3$H]-thymidine (20 Ci/mM; New England Nuclear) was added to each well and the cultures reincubated. Plates were then harvested with a Matrix filtermate harvester (Packard) and counted using an Automatic Direct Beta Counter (Packard). Mean cpm and the standard error of the mean were calculated from triplicate wells.

Figure 3:
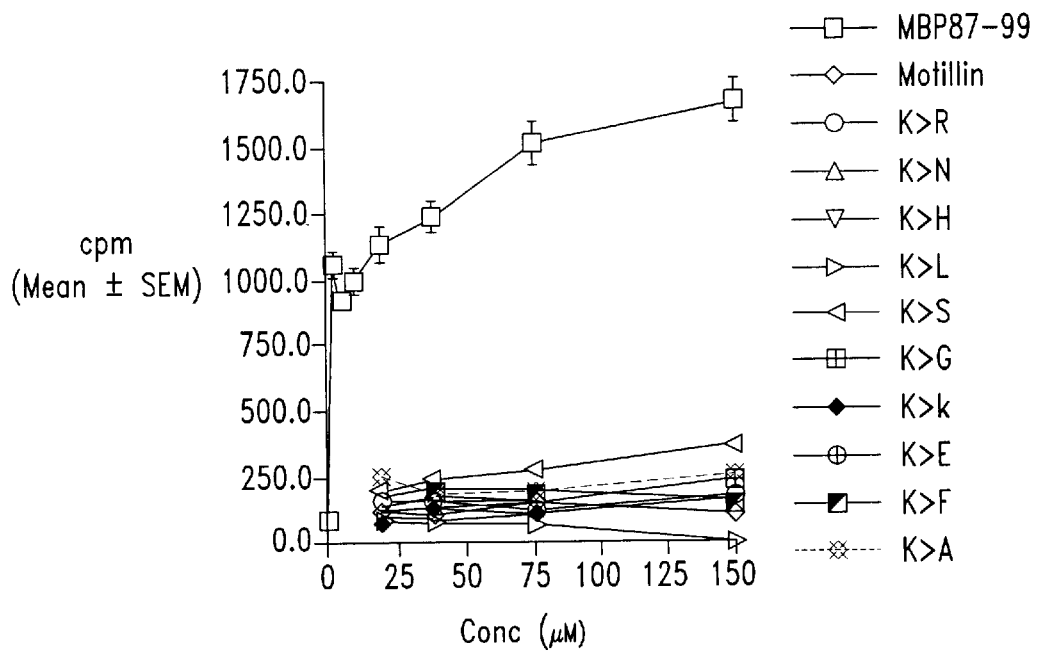
Figure 4:
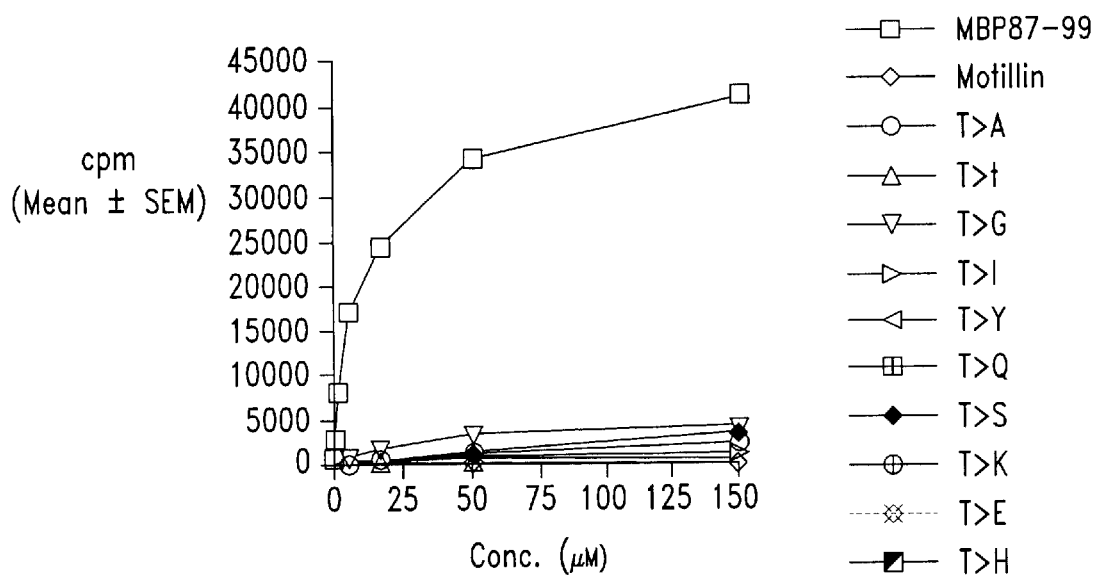
Figure 5:
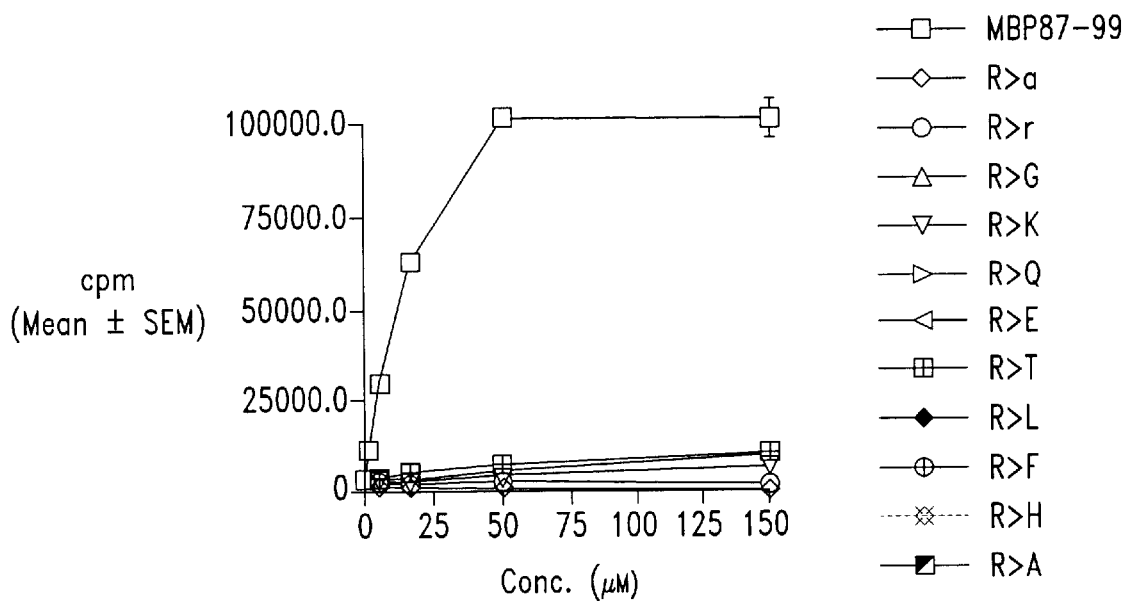

As can be seen in FIGS. 3, 4, and 5 a peptide analog with any substitution of position 91, 95, or 97 failed to stimulate proliferation of a MBP (87–99)-reactive T cell line. The effect was dramatic as even 150 μM of peptide analog was 1 to 2 logs less effective at causing proliferation.

EXAMPLE 7

Antagonism of T cell proliferation assay

T cell antagonism was detected in a prepulsed proliferation assay as described by De Magistris et al. (Cell 58:625, 1992) with minor modifications. Antigen presenting spleen cells were γ-irradiated (3000 rad) and incubated with shaking at a concentration of $10^7$ cells/well with 0.2–2.0 μM of the native peptide MBP (87–99) in stimulation medium in 10 ml tissue culture plates for 2 to 4 hours at 37° C. in humidified air containing 6.5% $CO_2$. Spleen cells were then washed and re-cultured at a concentration of $5 \times 10^5$ cells/well in U-shape 96-well microculture plates together with $5 \times 10^4$ resting MBP (87–99) reactive T cells. Various concentrations of antagonist peptides, ranging from 5–150 μM, were added for an additional 72 hours. Each well was pulsed with 0.5–1 μCi of [$^3$H]-thymidine (specific activity 10 Ci/mmol) for the final 12–16 hours. The cultures were then harvested on fiberglass filters and the proliferative response expressed as CPM±SEM.

Figure 6:
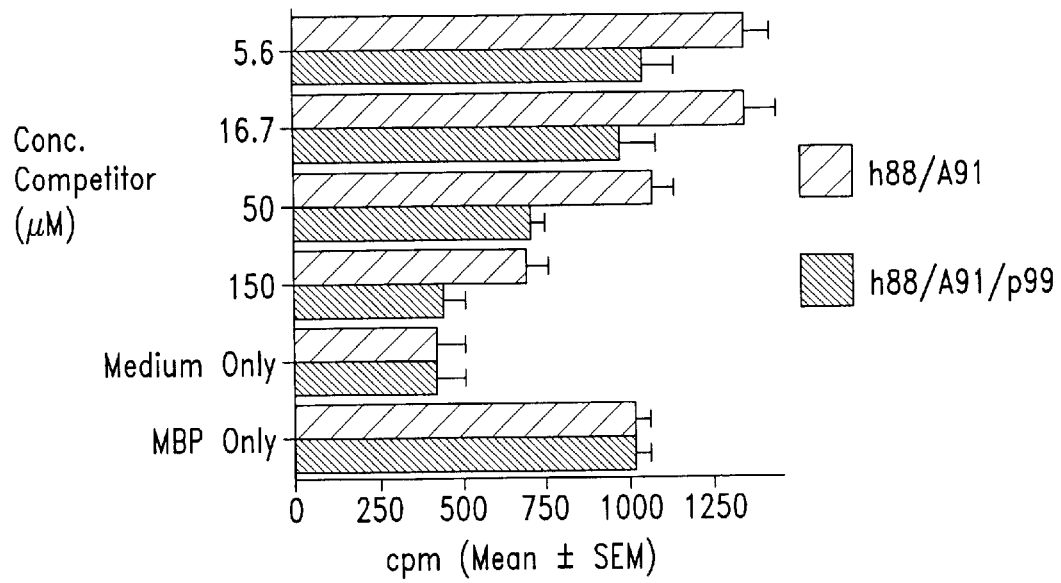

The data presented in FIG. 6 demonstrates that the double altered peptide analog, h88/A91, and the triple altered peptide analog, h88/A91/p99, significantly inhibited proliferation of a MBP reactive T cell line. The triple altered analog caused inhibition at 50 μM and higher concentration, while the double altered analog caused inhibition at 150 μM.

EXAMPLE 8

Treatment of 87–99 Induced EAE in Lewis Rats

Female Lewis rats, which were 6–8 weeks old, were injected with 500 μg of MBP (87–99) in CFA containing 500 μg of *Mycobacterium tuberculosis* at the base of the tail in 200 μl volume. Rats were divided in groups of 5. The control group received 0.5 ml of PBS and the treatment group received the h88/A91 peptide analog (1 mg/0.5 ml PBS) intraperitoneally, twice, on days 9 and 10 after immunization. Animals were monitored for disease symptoms on a daily basis. EAE was recorded on the following scale: 0, no symptoms; 1, tail paralysis; 2, hind limb weakness; 3, hind limb paralysis; 4, hind and front limbs affected.

Figure 7:
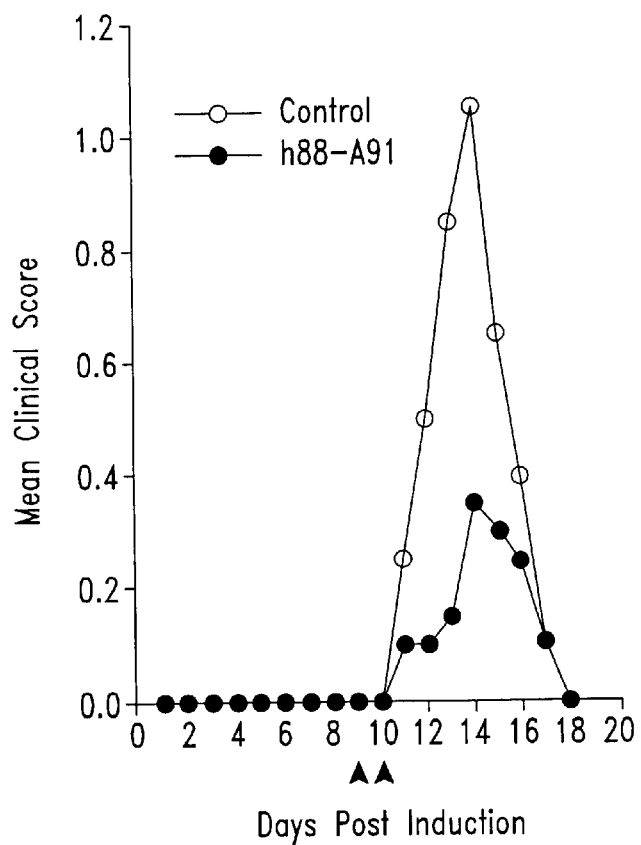

Data from two different experiments was obtained as mean cumulative score of 5 animals (FIG. 7). Untreated control animals went on to develop high level of disease whereas h88/A91 analog of the MBP peptide 87–99 was effective in preventing significantly the development of EAE in two experiments. Though the analog was given just before the onset of overt symptoms, it was able to arrest the development of EAE.

EXAMPLE 9

Induction of EAE by Peptide Analog

The ability of peptide analogs to cause EAE is assessed in vivo. Rats were injected with MNBP (87–99) or h88/A91 peptide analog as described in Example 2. Animals were monitored daily for evidence of EAE. Rats receiving MNBP (87–99) had 100% incidence (18/18 rats) of EAE with a mean maximum clinical score of 2.4±0.2. In contrast, 0/12 rats receiving the peptide analog h88/A91 had EAE. Therefore, this peptide analog does not induce EAE.

EXAMPLE 10

Treatment of EAE With Peptide Analogs

The 91K>A peptide analog is capable of inhibiting the adoptive transfer of disease by immune T cells in the Lewis rat strain (Karin et al., 1994). Further characterization of the effects of the peptide analog or altered peptide ligand (APL) on the immune system was investigated in Lewis rates injected with HBP.

In this system, experimental allergic encephalomyelitis (EAE) was induced in twelve female Lewis rats by injection of MBP(83–99) peptide in complete Freund's adjuvant (CFA) at the base of the tail. Nine days later, rats were divided into two groups of six animals and subcutaneously injected with 13.2 mg/kg of either peptide analog or a control peptide, sperm whale myoglobin (SWM) (110–121). Animals were monitored daily for disease symptoms and scored in a blinded fashion on a nonlinear ascending scale of 0–4 with increments denoting increasing paralysis. Each individual score was averaged with group cohorts to obtain the mean clinical score. The results from one such experiment are shown in FIG. 9.

Figures 8, 9:
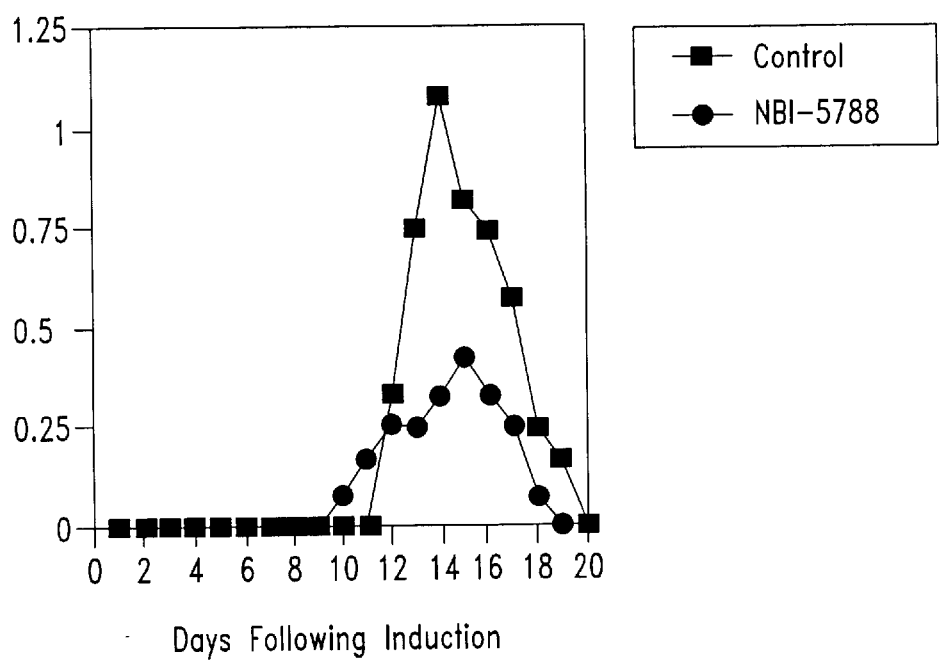
Figure 10:
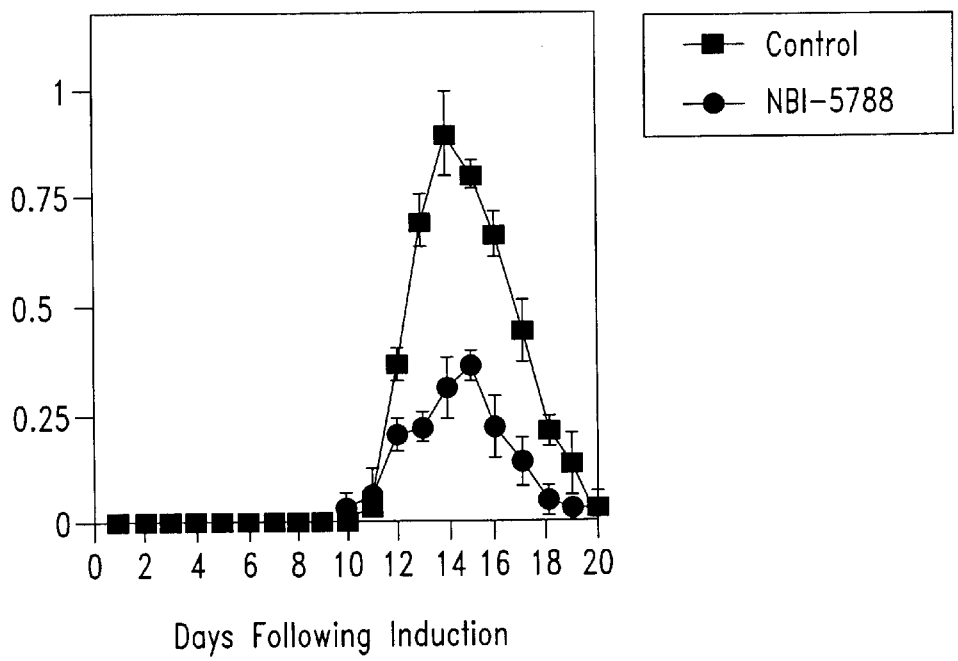
Figure 11:
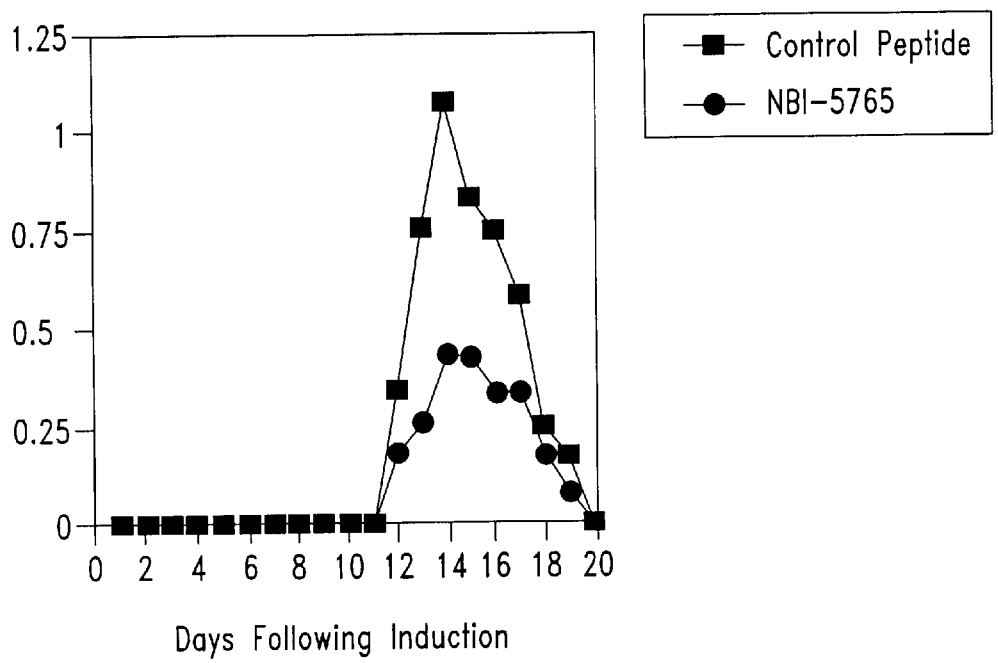

As seen in FIG. 9, the disease severity in those animals treated with the APL NBI-5788 (FIG. 8) was about 50% reduced compared to the control group. FIG. 10 shows the average disease severity of the results from three separate therapy experiments. The APL NBI-5788 significantly reduced the severity and duration of the disease in this model system. FIG. 11 shows the results from treatment using another APL, NBI-5765 (FIG. 8). This APL also significantly reduced the magnitude of the disease in the treated group over the control animals.

Although these results clearly demonstrate that APL inhibits the development of EAE, a murine animal model system of EAE has also been developed. The SJL/J. (H-$2^5$) mouse develops a chronic relapsing form of EAE in response to immunization with MBP(83–99) peptide in the presence of pertussis vaccine. The ability of the peptide analogs NBI-5719 (SEQ ID NO:4) and NBI-5765 (SEQ ID NO:6) to inhibit the disease was evaluated (see FIG. 12).

Figure 12:
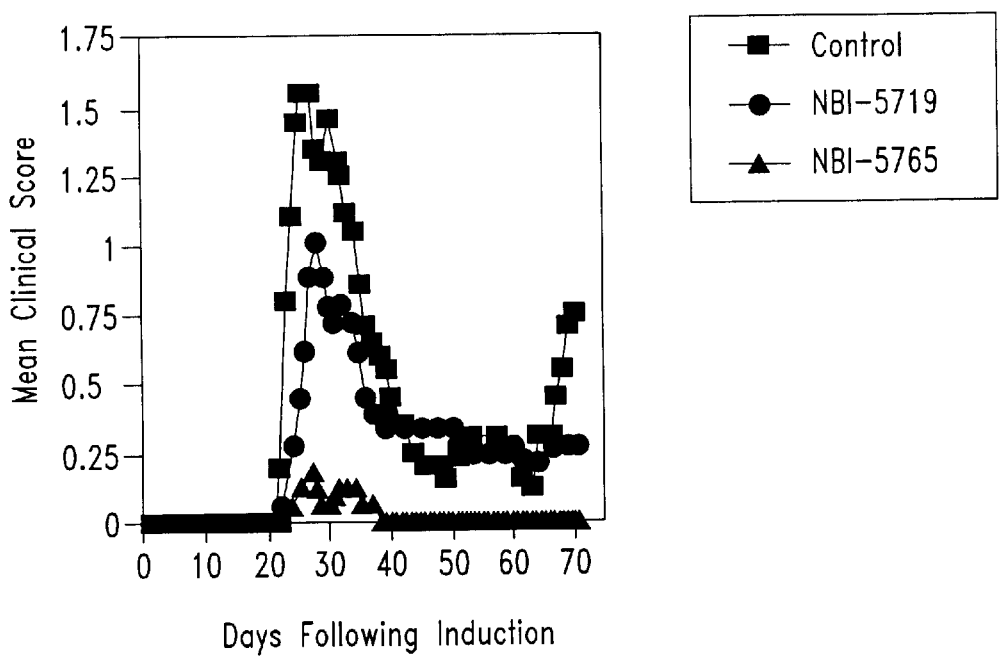

Groups of 10 animals were injected intraperitoneally weekly for 4 weeks with 20 mg/kg of either a control peptide or the peptide analog. The animals were then monitored for disease over the next 2–3 months. As can be seen in FIG. 12, SJL/J mice developed symptoms of EAE beginning around day 20 in the control group that lasted for approximately 3 weeks. Beginning around day 70, a relapse occurred reaching a mean clinical score of about 1. However, weekly injection with the APL NBI-5765 (SEQ ID NO:6) or NBI-5719 (SEQ ID NO:4) for four weeks not only reduced the level of the disease in the first phase, but also reduced the severity of the relapse. This is particularly striking since the animals had not been exposed to the APL for approximately one month.

EXAMPLE 11

Effects of Peptide Analogs on Human T Cell Proliferation

The ability of the peptide analogs NBI-5719, 5748, 5765, 5788 and 5789 (SEQ ID NOs:4–8 respectively) to affect human T cell proliferation was assessed. A constant amount of peptide analog or the control peptide SWM (50 $\mu$M) was cultured with varying concentrations of native MBP(83–99) peptide (1.1–30 $\mu$M) in the presence of irradiated, DR matched peripheral blood cells and T cell clones derived from various MS patients. Human T cells ($1 \times 10^6$) were cultured with DR matched, irradiated peripheral blood cells (PBL, $5 \times 10^6$) in medium containing IMDM supplemented with 3 $\mu$M MBP83–99, 2 mM L-glutamine, 50 $\mu$g/ml gentamicin penicillin/streptomycin, 100 U/ml rIL-2 and 10% human AB-negative serum. Cells were cultured for approximately 60 hours, pulsed with tritiated thymidine for 12 hours, and harvested. The amount of tritiated thymidine incorporated was measured, and the data represented as the mean plus or minus the standard error of the mean of replicate samples. Representative results are shown in FIGS. 13 and 14.

Figure 13:
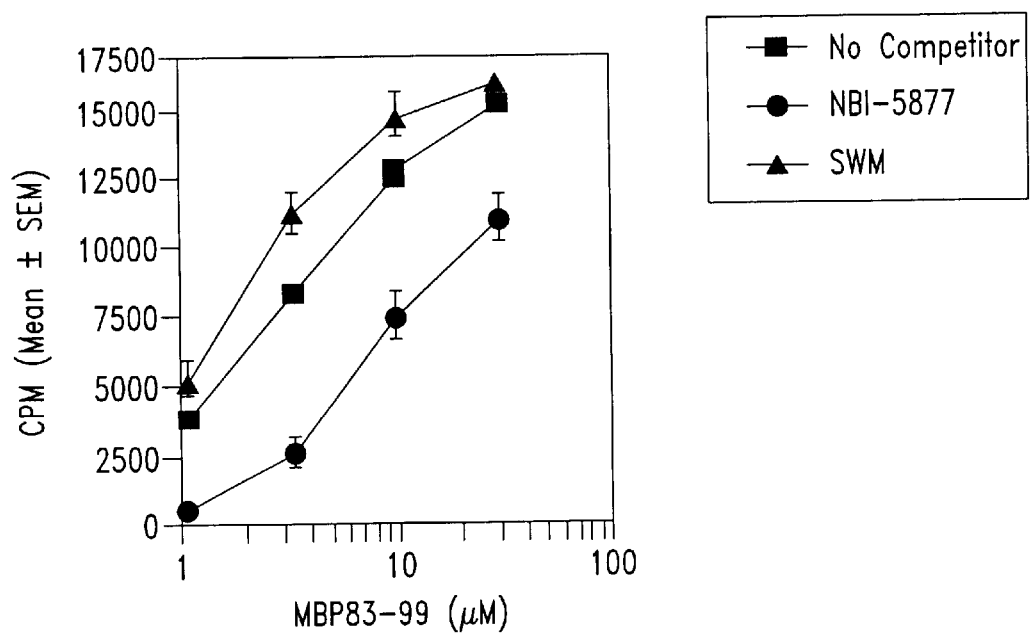
FIG. 13 is a graph illustrating the ability of a peptide analog of MBP to inhibit proliferation of a Dr2a restricted human T cell clone, which is reactive to MBP. The proliferative response of the T cell clone incubated with varying concentrations of MBP (83–99) and 50 micromolar of either the peptide analog or sperm whale myoglobin, the control peptide, is depicted.
Figure 14:
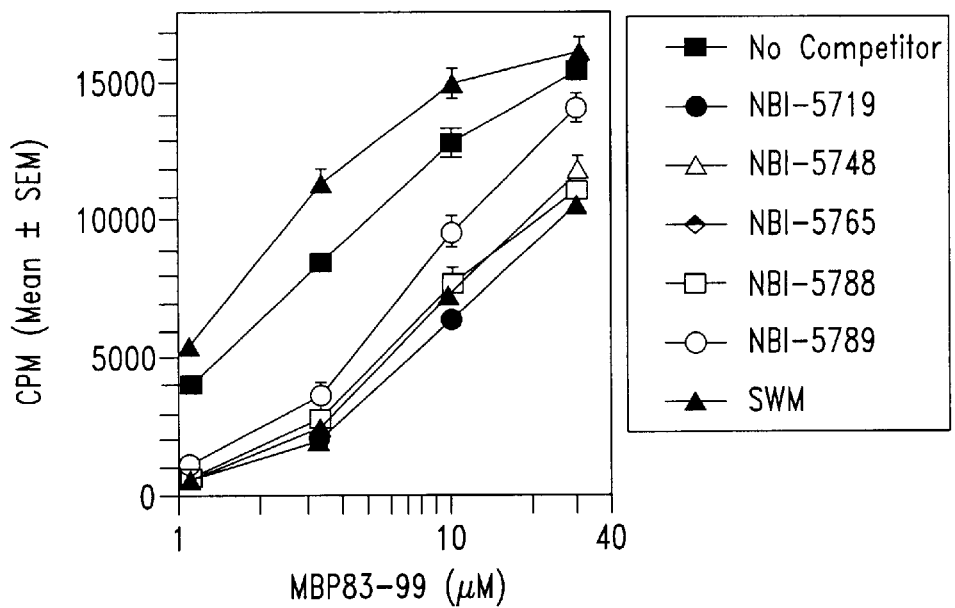
FIG. 14 is a graph illustrating the ability of peptide analogs of MBP to inhibit proliferation of a Dr2a restricted human T cell clone, which is reactive to MBP. The proliferative response of the T cell clone incubated with varying concentrations of MNBP (83–99) and 50 micromolar of either the peptide analog or sperm whale myoglobin, the control peptide, is depicted.

As seen in FIG. 13, the peptide analog NBI-5788 (SEQ ID NO:7) corresponding to MBP(83–99) (83E>a, 84N>K, 89F>L, and 91K>A) inhibited the ability of a human Dr2a restricted T cell clone to respond to varying concentrations of MBP(83–99), where the irrelevant peptide (sperm whale myoglobin, SWM 110–121) had little effect on the proliferative capacity of the T cells. FIG. 14 shows that all the peptides inhibited the ability of the Dr2a restricted T cells to respond to native MBP peptide in a concentration dependent fashion.

Figure 15:
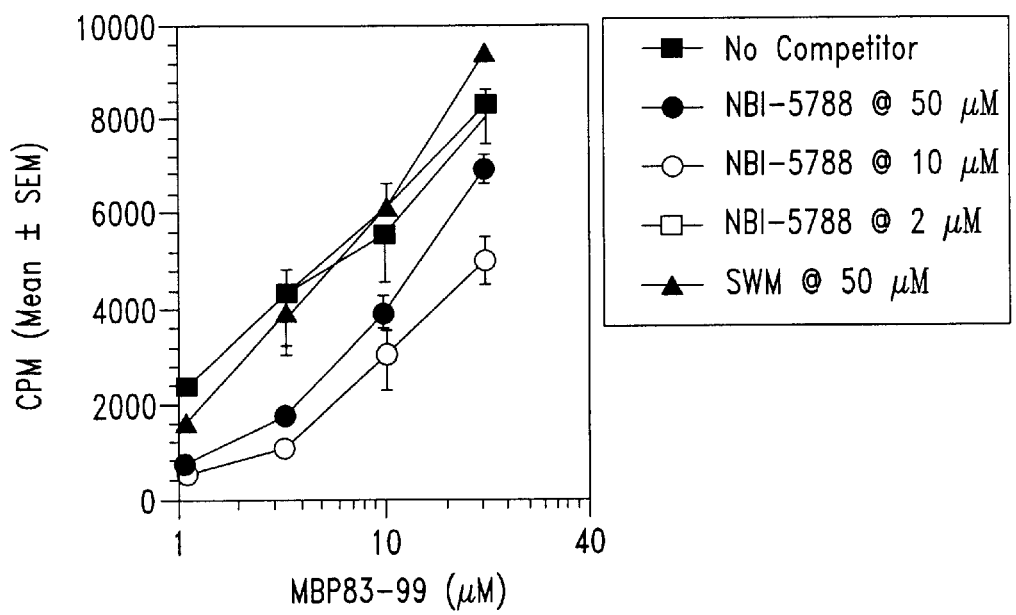
FIG. 15 is a graph illustrating the ability of a peptide analog of MBP to inhibit proliferation of a Dr2a restricted human T cell clone, which is reactive to MBP. The proliferative response of the T cell clone incubated with varying concentrations of MBP (83–99) at various concentrations of the peptide analog or 50 micromolar sperm whale myoglobin, the control peptide, is depicted.

The potency of NBI-5788 (SEQ ID NO:7) was then determined by varying concentrations of the APL (2, 10, or 50 $\mu$M) in the presence of varying amounts of the native mBP(83–99) (1.1–30 $\mu$M). As seen in FIG. 15, at both 10 and 50 $\mu$M, NBI-5788 (SEQ ID NO:7) significantly altered the ability of the Dr2a T cell line to respond to NBP(83–99), but no significant inhibition was seen with the irrelevant peptide SWM.

The ability of the peptide analog to inhibit the proliferative response of MBP-reactive T cells isolated from Dr2b (DrB 1*1501) individuals was determined. A constant amount of NBI-5788 (50 $\mu$M) was cultured with varying concentrations of native peptide (1.1–30 $\mu$M) in the presence of irradiated, DR matched peripheral blood cells and T cell clones derived from various MS patients.

Figure 16:
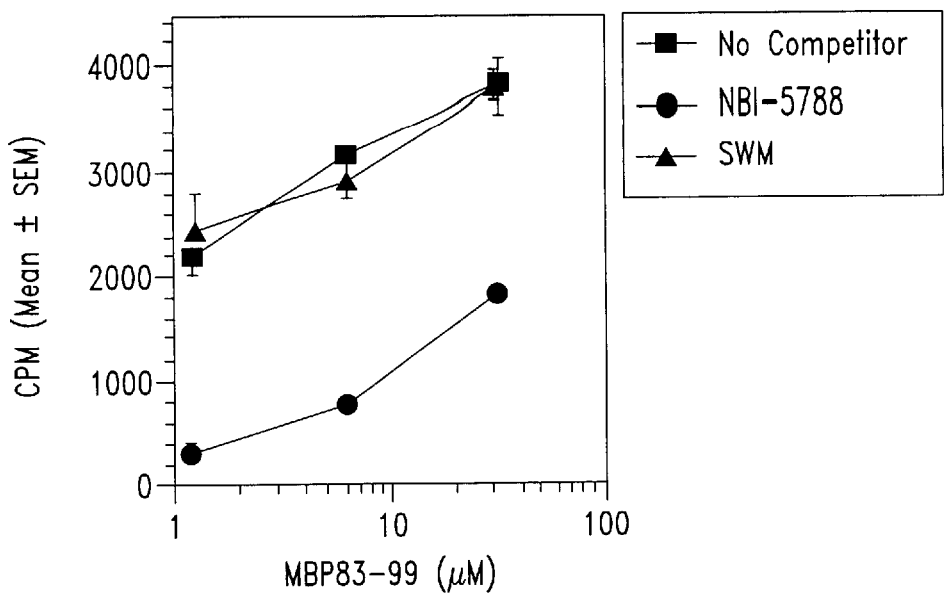
FIG. 16 is a graph illustrating the ability of a peptide analog of MBP to inhibit proliferation of a Dr2b restricted human T cell clone, which is reactive to MBP. The proliferative response of the T cell clone incubated with varying concentrations of MBP (83–99) and 50 micromolar of either the peptide analog or sperm whale myoglobin, the control peptide, is depicted.
Figure 17:
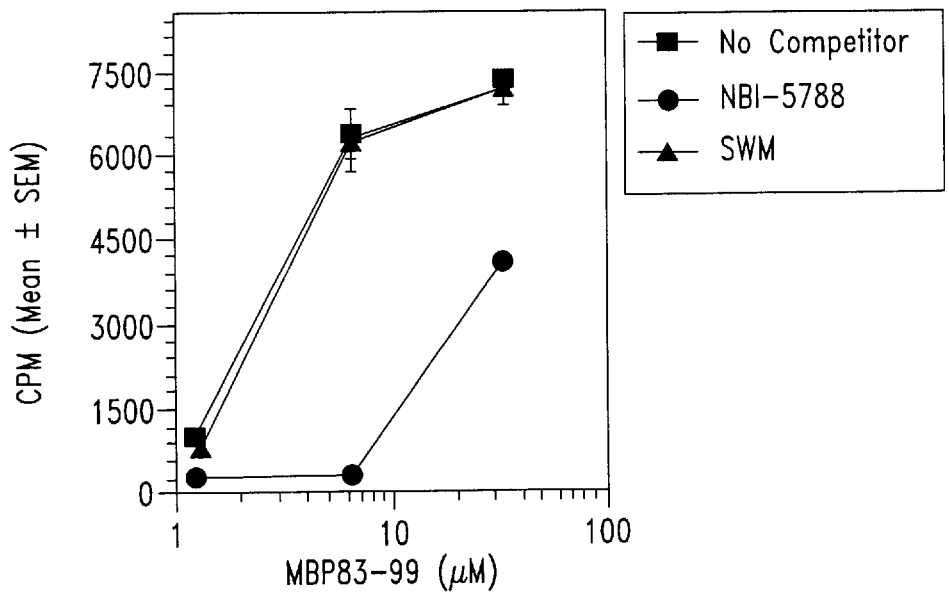
FIG. 17 is a graph illustrating the ability of a peptide analog of MBP to inhibit proliferation of a Dr2b restricted human T cell clone, which is reactive to MBP. The proliferative response of the T cell clone incubated with varying concentrations of MBP (83–99) and 50 micromolar of either the peptide analog or sperm whale myoglobin, the control peptide, is depicted.
Figure 18:
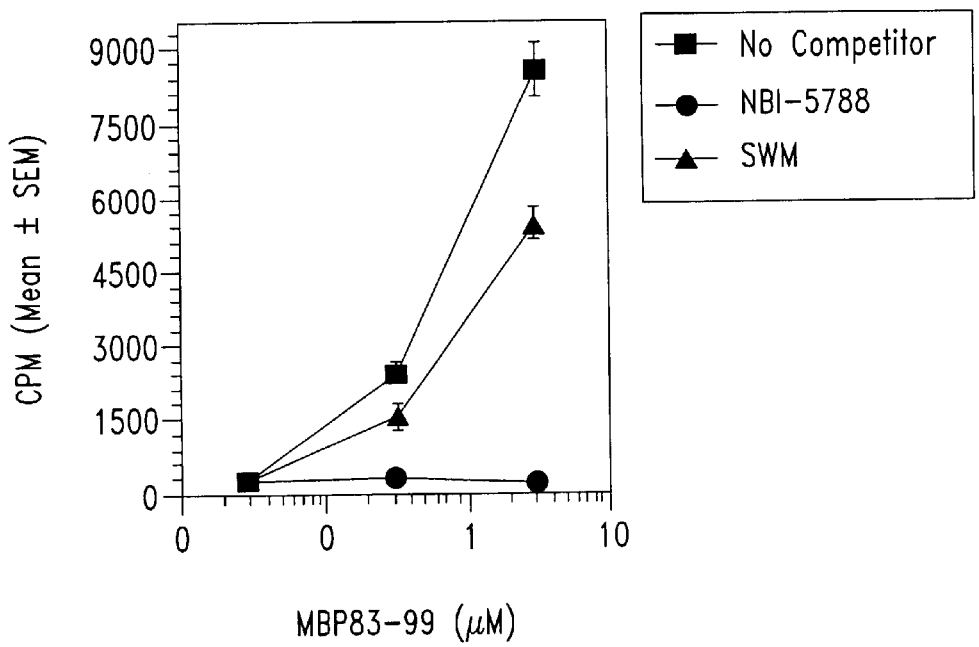
FIG. 18 is a graph illustrating the ability of a peptide analog of MBP to inhibit proliferation of a Dr2b restricted human T cell clone, which is reactive to MBP. The proliferative response of the T cell clone incubated with varying concentrations of M1BP (83–99) and 50 micromolar of either the peptide analog or sperm whale myoglobin, the control peptide, is depicted.

FIGS. 16, 17, and 18 depict results using three different T cell lines. Each T cell clone varies in the amount of thymidine incorporated in response to MBP peptide. Nevertheless, NBI-5788 (SEQ ID NO:7) inhibited the ability of the T cell clones to respond to MBP peptide in a concentration dependent fashion. The irrelevant peptide SWM had little influence on the ability of the T cells to respond to MBP peptide.

Figure 19:
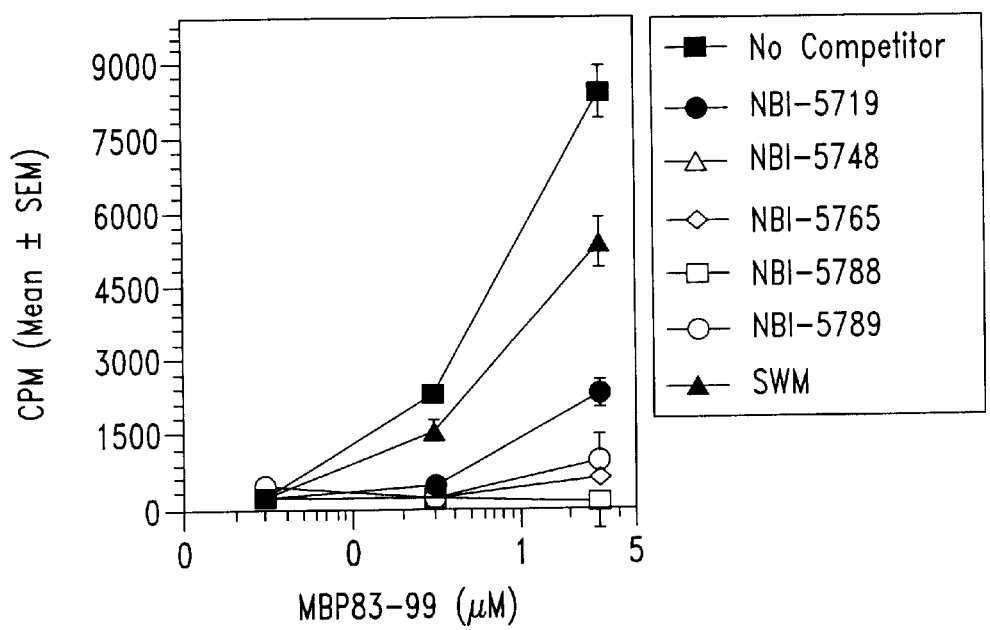
FIG. 19 is a graph illustrating the ability of a peptide analog of MBP to inhibit proliferation of a Dr2b restricted human T cell clone, which is reactive to MBP. The proliferative response of the T cell clone incubated with varying concentrations of MBP (83–99) and 50 micromolar of either the peptide analog or sperm whale myoglobin, the control peptide, is depicted.

FIG. 19 depicts the ability of NBI-5719 (SEQ ID NO:4), NBI-5748 (SEQ ID NO:5), NBI-5765 (SEQ ID NO:6), NBI-5788 (SEQ ID NO:7), and NBI-5789 (SEQ ID NO:8) to inhibit the MBP-dependent proliferation of the Dr2b restricted human T cell clone 5F6. As seen above with the Dr2b restricted T cells (FIG. 14), the APL inhibited the MBP-dependent proliferation in a concentration dependent fashion. However, the control peptide SWM had little effect on the proliferative response.

Figure 20:
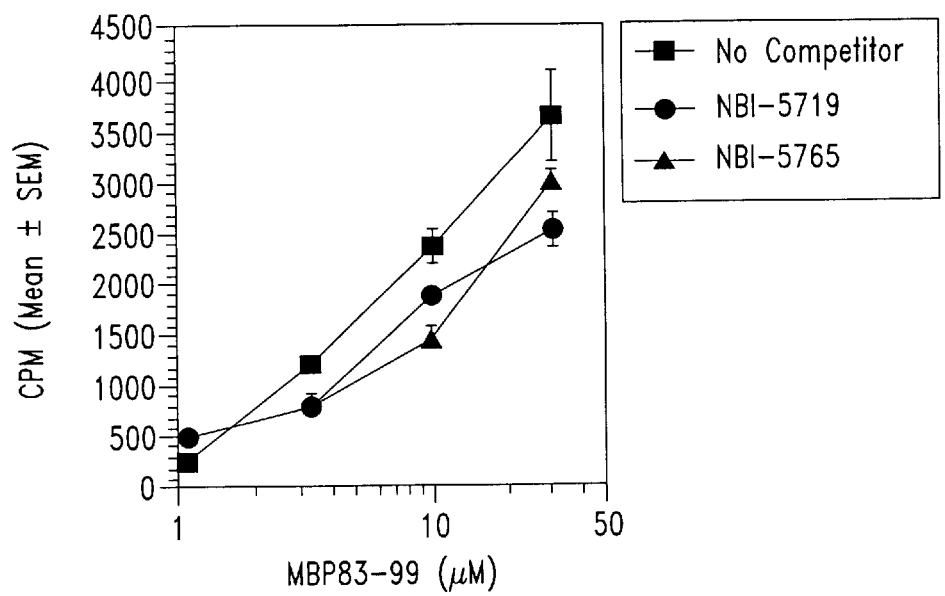
FIG. 20 is a graph illustrating the ability of a peptide analog of MBP to inhibit proliferation of a Dr2b restricted human T cell clone, which is reactive to MBP. The proliferative response of the T cell clone incubated with varying concentrations of MBP (83–99) and 50 micromolar of either the peptide analog or sperm whale myoglobin, the control peptide, is depicted.

FIG. 20 depicts the ability of NBI-5719 (SEQ ID NO:4) and NBI-5765 (SEQ ID NO:6) to inhibit the MBP-dependent proliferation of the Dr4 Dw4 restricted human T cell clone MS-1. As seen above with the Dr2 restricted T cells, the APL inhibited the MBP-dependent proliferation in a concentration dependent fashion.

The ability of the peptide analog ligand to influence cytokine production was next measured. The Dr2b-restricted T cell clone 5F6 was incubated in the presence of 3 $\mu$M MBP peptide with either 10 $\mu$M of NBI-5788 (SEQ ID NO:7) or SWM or medium only. As a control, cells were cultured in the presence of medium alone. After 24 hours, supernatants were removed and the levels of tumor necrosis factor alpha (TNF-$\alpha$) and interferon-$\gamma$ (IFN-$\gamma$) determined using commercially available EIA kits.

As can be seen in FIG. 21, MBP stimulated the production of both TNF-$\alpha$ and IFN-$\gamma$ (approximately 200 and 160 pg/ml, respectively). However, the peptide analog ligand NBI-5788 (SEQ ID NO:7) dramatically inhibited the production of both pro-inflammatory cytokines to approximately levels achieved with medium only. The irrelevant peptide SWM had minimal effect on cytokine production. None of the peptide analogs NBI-5719 (SEQ ID NO:4), NBI-5748 (SEQ ID NO:5), NBI-5765 (SEQ ID NO:6), NBI-5788 (SEQ ID NO:7), or NBI-5789 (SEQ ID NO:8) stimulated cytokine production over background, even at concentrations of 50 $\mu$M (data not shown).

EXAMPLE 12

Induction of Peptide Analog-specific T cells

This example illustrates the generation of a cellular immune response in patients following administration of APL NBI-5788(SEQ ID NO:7), corresponding to MBP (83–99) (83E>a, 84N>K, 89F>L, and 91K>A).

Patients received either 10 or 20 mg of APL NBI-5788 (weekly for four weeks). Peripheral blood cells were collected from four patients approximately one year after dosing, as well as from 14 MS patients who had not received the APL and from two normal, healthy volunteers. The frequency of response to the peptide was determined using the split-well technique. Cells were seeded in 48 wells/plate, as well as 12 control wells without antigenic stimulation, at a density of 1×10$^5$ cells/well. Cells were set up in IMDM+ 10% human plasma pool+penicillin/streptomycin 100 U/ml+gentamycin 50 $\mu$g/ml+2 mM L-glutamine (or complete media, CM). Peptide antigen (25 $\mu$g) was added and then included for no more than one feeding with media. At day 12, the medium was changed to CM without IL-2. Two days later, the split-wells were established. The wells were resuspended with a multichannel pipetor, 100 $\mu$l of the cell suspension was transferred to adjacent wells on a new plate (daughter plate) and mixed with 100 $\mu$l of media containing 1×10$^5$ antigen presenting cells (peripheral blood lymphocytes, PBL irradiated with 3000 R in CM with or without antigen; 25 $\mu$g/ml). After 48 hours of culturing, 100 $\mu$l of supernatant was removed from the daughter plate for later cytokine determination and stored at −70° C.

For the proliferation assay, $^3$H-thymidine (0.5 $\mu$Ci) was added to the daughter plate and the plates reincubated for an additional 8 hours. The wells were then harvested onto filter mats and the level of $^3$H-thymidine incorporation determined using beta scintillation. Counts greater than three-fold over background were considered positive.

The frequency of APL responsive wells (SI>3) for the three patients treated with 20 mg of APL was 11, 32 and 72%, and 23% for the patient who received 10 mg (FIG. 22). Mean frequency for all controls was 10±2%, n=14. APL specific cell lines were subsequently generated by repeated co-culture with APL antigen; 6/31 lines from treated patients cross reacted with native MBP 83–99; 4/31 reacted with whole MBP. Three of the 23 APL lines from untreated MS patients cross-reacted with MBP peptide 83–99; two of the 23 reacted with whole MBP. The cross reactivity is shown in Tables 1 and 2.

TABLE 1

Frequency and Cross-reactivity of APL NBI-5788-reactive T Cells Isolated from MS Patients

| Treatment Group | Percent Reactivity |
| --- | --- |
| APL NBI-5788 20 mg (n = 3) | 39 ± 18 |
| APL NBI-5788 10 mg (n = 1) | 23 |
| MS Controls (n = 14) | 10 ± 2 |

TABLE 2

Frequency and Cross-reactivity of APL NBI-5788-reactive T Cells Isolated from MS Patients

| | Percent Cross Reactivity | |
| --- | --- | --- |
| Treatment Group | Whole MBP | MPB Peptide |
| APL NBI-5788 20 mg (n = 3) | 17 (4/24) | 17 (4/24) |
| APL NBI-5788 10 mg (n = 1) | 0 (0/7) | 29 (2/7) |
| MS Controls (n = 14) | 9 (2/23) | 13 (3/23) |

The results indicate that administration of 10–20 mg of the APL weekly for four weeks generated a persistent systemic immune response. The response was polyclonal in nature, with some of the responding cells being specific for the APL and others cross-reactive to both the native and altered peptide.

EXAMPLE 13

Functional Phenotype of T Cells Induced by Peptide Analog

This example illustrates the functional phenotype of T cells induced by the representative peptide analog APL NBI-5788.

Four cell cultures from one patient (LW, 32% frequency) showing a response (>three-fold over background) were expanded into cell lines (LW 80, 88, 90 and 93) by incubation in IL-2 for 11–14 days (1–2 passages). Once sufficient cells had grown up, they were cultured with either medium alone or 25 $\mu$g/ml of either whole MNBP, MBP (83–99) or APL NBI-5788. After 24 hours, the supernatants were collected and the level of cytokines determined (see FIGS. 22 to 26). The remaining cultures were pulsed with radiolabeled thymidine and the extent of incorporation determined. The results, expressed as the mean in cpm±the standard error of the mean are presented in Table 3.

TABLE 3

Specificity of APL 5788 Reactive T Cells Isolated from Patient LW

| Line | Medium Only | Whole MBP | MBP (83–99) | NBI 5788 |
|------|-------------|-----------|-------------|----------|
| 80 | 940 ± 87 | 1,457 ± 195 | 1,509 ± 1,106 | 25,696 ± 408 |
| 88 | 1,590 ± 199 | 977 ± 121 | 1,033 ± 112 | 11,603 ± 424 |
| 90 | 1,047 ± 18 | 1,604 ± 328 | 1,272 ± 192 | 25,317 ± 8,221 |
| 93 | 557 ± 2 | 630 ± 28 | 898 ± 643 | 16,197 ± 2,095 |

These results demonstrate that immune response generated by administration of 10–20 mg of the APL weekly for four weeks appears to be Th2 in nature. In particular, the extent of interleukin 5 and 13 that was produced is consistent with a Th2 type response.

EXAMPLE 14

Protective Effect of Th2 Cells Specific for a Representative Peptide Analog

This example illustrates the ability of T cells specific for a representative peptide analog to confer a protective effect.

SJL mice were immunized with peptide analog, also referred to as an altered peptide ligand (APL), in which position 91 has been altered to alanine. This immunization resulted in a Th2 response. Th2-APL-specific cells were isolated from the mouse lymph nodes and cultured. These cultured Th2-APL-specific cells were then introduced into animals in which EAE had been induced. To induce EAE, SJL/J female mice (5 per group) were injected in the base of the tail with MBP (83–99) (250 μg) on Day 0, and on Day 6 with proteolipid peptide (PLP 139–151), both emulsified in incomplete Freund's adjuvant (DIFCO, Detroit, Mich.) to which 10 (Day 0) or 2 mg/ml (Day 6) of heat killed Mycobacterium H37Ra was added. Mice also received intravenously 200 ng (in 200 μl PBS) of Bordelella pertussis toxin on Day 6 and Day 8. On Day 7, animals were given 30×10$^6$ Th2-APL-specific cells, or as a control syngeneic spleen cells, intravenously and the effect on disease was monitored. This effect, shown as mean clinical score, is presented in FIG. 27.

The surprising results of this experiment show that administration of APL-specific Th2 cells result in a very strong reduction in the disease and accordingly confer resistance. The Th2-APL-specific cells appear to be central to the protective effect. Animals receiving control cells exhibited a relapsing/remitting type of disease characteristic of PLP. Animals receiving the APL-reactive Th2 cells had significantly less disease throughout the course of the experiment, and the protection seen in the relapse phase of the disease (day 50–75) was even more impressive than that seen in the primary phase. These results indicate that an APL that comprises an alteration at position 91 and analogs thereof have a protective effect.

EXAMPLE 15

Induction of Th2 Response by a Representative Peptide Analog

This example illustrates the induction of a Th2 response in SJL mice by administration of APL NBI-5788, corresponding to MBP(83–99) (83E>a, 84N>K, 89F>L, and 91K>A).

SJL/J. female mice (3 per group) were injected weekly on days 0, 7, 14 and 21 subcutaneously with 20 mg/kg of NBI-5788 in the flanks. On day 28, the mice were sacrificed, the draining lymph node removed, a single cell suspension was made and the ability of the cells to proliferate in response to 25 μM NBI-5788 was determined. The data, shown in FIG. 28, represent the mean of triplicate wells.

The results show that repeated dosing with NBI 5788 induces a Th2 response in the animal model as measured by T-cell proliferation ex vivo, in the presence of NBI 5788. The four subsequent doses which were made at weekly intervals each resulted in a stronger response after each subsequent dose.

From the foregoing, it will be evident that although specific embodiments of the invention have been described herein for the purpose of illustrating the invention, various modifications may be made without deviating from the spirit and scope of the invention.

What is claimed is:

1. A method for inducing a Th2 immune response to myelin basic protein or a peptide analog thereof in a patient, comprising:

administering to a patient a composition comprising a peptide analog comprising contiguous residues 83–99 of human myelin basic protein, wherein the L-glutamic acid at position 83 is altered to D-alanine, L-asparagine at position 84 is altered to L-lysine, L-phenylalanine at position 89 is altered to L-leucine, and L-lysine at position 91 is altered to L-alanine, wherein the peptide analog is administered in combination with a physiologically acceptable carrier or diluent.

2. The method of claim 1, wherein the composition further comprises an adjuvant.

3. The method of claim 2, wherein the adjuvant is alum.

* * * * *

SEQUENCE LISTING

```
<160> NUMBER OF SEQ ID NOS: 8

<210> SEQ ID NO 1
<211> LENGTH: 516
<212> TYPE: DNA
<213> ORGANISM: Homo sapiens
<220> FEATURE:
<221> NAME/KEY: CDS
<222> LOCATION: (4)..(513)

<400> SEQUENCE: 1 atg gcg tca cag aag aga ccc tcc cag agg cac gga tcc aag tac ctg      48
Met Ala Ser Gln Lys Arg Pro Ser Gln Arg His Gly Ser Lys Tyr Leu
 -1   1               5                  10                  15 gcc aca gca agt acc atg gac cat gcc agg cat ggc ttc ctc cca agg      96
Ala Thr Ala Ser Thr Met Asp His Ala Arg His Gly Phe Leu Pro Arg
                20                  25                  30 cac aga gac acg ggc atc ctt gac tcc atc ggg cgc ttc ttt ggc ggt     144
His Arg Asp Thr Gly Ile Leu Asp Ser Ile Gly Arg Phe Phe Gly Gly
```

|  |  |  |  |  |  |  |  |  |  |  |  |  |  |  |  |
|---|---|---|---|---|---|---|---|---|---|---|---|---|---|---|---|
|  |  |  | 35 |  |  |  | 40 |  |  |  |  | 45 |  |  |  |
| gac | agg | ggt | gcg | cca | aag | cgg | ggc | tct | ggc | aag | gac | tca | cac | cac | ccg |
| Asp | Arg | Gly | Ala | Pro | Lys | Arg | Gly | Ser | Gly | Lys | Asp | Ser | His | His | Pro |
|  |  |  | 50 |  |  |  | 55 |  |  |  |  | 60 |  |  |  |

192 gca aga act gct cac tat ggc tcc ctg ccc cag aag tca cac ggc cgg        240
Ala Arg Thr Ala His Tyr Gly Ser Leu Pro Gln Lys Ser His Gly Arg
     65              70                  75 acc caa gat gaa aac ccc gta gtc cac ttc ttc aag aac att gtg acg        288
Thr Gln Asp Glu Asn Pro Val Val His Phe Phe Lys Asn Ile Val Thr
 80              85                  90                      95 cct cgc aca cca ccc ccg tcg cag gga aag ggg aga gga ctg tcc ctg        336
Pro Arg Thr Pro Pro Pro Ser Gln Gly Lys Gly Arg Gly Leu Ser Leu
             100                 105                 110 agc aga ttt agc tgg ggg gcc gaa ggc cag aga cca gga ttt ggc tac        384
Ser Arg Phe Ser Trp Gly Ala Glu Gly Gln Arg Pro Gly Phe Gly Tyr
         115                 120                 125 gga ggc aga gcg tcc gac tat aaa tcg gct cac aag gga ttc aag gga        432
Gly Gly Arg Ala Ser Asp Tyr Lys Ser Ala His Lys Gly Phe Lys Gly
     130                 135                 140 gtc gat gcc cag ggc acg ctt tcc aaa att ttt aag ctg gga gga aga        480
Val Asp Ala Gln Gly Thr Leu Ser Lys Ile Phe Lys Leu Gly Gly Arg
145                 150                 155 gat agt cgc tct gga tca ccc atg gct aga cgc tga                        516
Asp Ser Arg Ser Gly Ser Pro Met Ala Arg Arg
160                 165                 170

<210> SEQ ID NO 2
<211> LENGTH: 171
<212> TYPE: PRT
<213> ORGANISM: Homo sapiens

<400> SEQUENCE: 2

Met Ala Ser Gln Lys Arg Pro Ser Gln Arg His Gly Ser Lys Tyr Leu
 1               5                  10                  15

Ala Thr Ala Ser Thr Met Asp His Ala Arg His Gly Phe Leu Pro Arg
             20                  25                  30

His Arg Asp Thr Gly Ile Leu Asp Ser Ile Gly Arg Phe Phe Gly Gly
         35                  40                  45

Asp Arg Gly Ala Pro Lys Arg Gly Ser Gly Lys Asp Ser His His Pro
     50                  55                  60

Ala Arg Thr Ala His Tyr Gly Ser Leu Pro Gln Lys Ser His Gly Arg
 65                  70                  75                  80

Thr Gln Asp Glu Asn Pro Val Val His Phe Phe Lys Asn Ile Val Thr
                 85                  90                  95

Pro Arg Thr Pro Pro Pro Ser Gln Gly Lys Gly Arg Gly Leu Ser Leu
            100                 105                 110

Ser Arg Phe Ser Trp Gly Ala Glu Gly Gln Arg Pro Gly Phe Gly Tyr
        115                 120                 125

Gly Gly Arg Ala Ser Asp Tyr Lys Ser Ala His Lys Gly Phe Lys Gly
    130                 135                 140

Val Asp Ala Gln Gly Thr Leu Ser Lys Ile Phe Lys Leu Gly Gly Arg
145                 150                 155                 160

Asp Ser Arg Ser Gly Ser Pro Met Ala Arg Arg
                165                 170

<210> SEQ ID NO 3
<211> LENGTH: 17
<212> TYPE: PRT

```
<213> ORGANISM: Artificial Sequence
<220> FEATURE:
<223> OTHER INFORMATION: Description of Artificial Sequence: Solid Phase
      Synthesis

<400> SEQUENCE: 3

Glu Asn Pro Val Val His Phe Phe Lys Asn Ile Val Thr Pro Arg Thr
 1               5                   10                  15

Pro

<210> SEQ ID NO 4
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: Where Xaa is an D-alanine residue
<220> FEATURE:
<221> NAME/KEY: MOD_RES
<222> LOCATION: (16)
<223> OTHER INFORMATION: Where Xaa is a D-alanine residue
<220> FEATURE:
<223> OTHER INFORMATION: Description of Artificial Sequence: Solid Phase
      Synthesis

<400> SEQUENCE: 4

Xaa Lys Pro Val Val His Ala Phe Ala Asn Ile Val Thr Pro Arg Xaa
 1               5                   10                  15

Pro

<210> SEQ ID NO 5
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: Where Xaa is a D-alanine residue
<220> FEATURE:
<221> NAME/KEY: MOD_RES
<222> LOCATION: (16)
<223> OTHER INFORMATION: Where Xaa is a D-alanine residue
<220> FEATURE:
<223> OTHER INFORMATION: Description of Artificial Sequence: Solid Phase
      Synthesis

<400> SEQUENCE: 5

Xaa Lys Pro Val Val His Leu Phe Ala Asn Ile Val Thr Pro Arg Xaa
 1               5                   10                  15

Pro

<210> SEQ ID NO 6
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: Where Xaa is a D-alanine residue
<220> FEATURE:
<223> OTHER INFORMATION: Description of Artificial Sequence: Solid Phase
      Synthesis

<400> SEQUENCE: 6

Xaa Asn Pro Val Val His Ala Phe Ala Asn Ile Val Thr Pro Arg Thr
 1               5                   10                  15

Pro
```

-continued

```
<210> SEQ ID NO 7
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: Where Xaa is a D-alanine residue
<220> FEATURE:
<223> OTHER INFORMATION: Description of Artificial Sequence: Solid Phase
      Synthesis

<400> SEQUENCE: 7

Xaa Lys Pro Val Val His Leu Phe Ala Asn Ile Val Thr Pro Arg Thr
  1               5                  10                  15

Pro

<210> SEQ ID NO 8
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: Where Xaa is a D-alanine residue
<220> FEATURE:
<223> OTHER INFORMATION: Description of Artificial Sequence: Solid Phase
      Synthesis

<400> SEQUENCE: 8

Xaa Lys Pro Val Val His Ala Phe Ala Asn Ile Val Thr Pro Arg Thr
  1               5                  10                  15

Pro
```